(12) United States Patent
Leopold et al.

(10) Patent No.: US 6,492,410 B1
(45) Date of Patent: Dec. 10, 2002

(54) COMBINATIONS OF PROTEIN FARNESYLTRANSFERASE AND HMG COA REDUCTASE INHIBITORS AND THEIR USE TO TREAT CANCER

(75) Inventors: Judith Leopold, Ann Arbor, MI (US); Roger Schofield Newton, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 09/674,818

(22) PCT Filed: May 10, 1999

(86) PCT No.: PCT/US99/10188

§ 371 (c)(1),
(2), (4) Date: Nov. 6, 2000

(87) PCT Pub. No.: WO99/58505

PCT Pub. Date: Nov. 18, 1999

Related U.S. Application Data

(60) Provisional application No. 60/085,202, filed on May 12, 1998, and provisional application No. 60/092,253, filed on Jul. 10, 1998.

(51) Int. Cl.$^7$ .............................................. A61K 31/415
(52) U.S. Cl. .................. 514/399; 514/311; 514/94; 514/18; 514/19; 514/400
(58) Field of Search .............................. 514/18, 19, 94, 514/311, 399, 400

(56) References Cited

U.S. PATENT DOCUMENTS 5,571,792 A   11/1996   Bolton et al. .................. 514/18

FOREIGN PATENT DOCUMENTS

| EP | 9310918 | 4/1989 |
| WO | 97/00895 | 1/1997 |
| WO | 98/57633 | 12/1998 |

*Primary Examiner*—James H. Reamer
(74) *Attorney, Agent, or Firm*—Michael J. Atkins; Heidi M. Berven; Francis J. Tinney

(57) ABSTRACT

Novel combinations of inhibitors of protein farnesyltransferase enzymes and HMG CoA reductases enzymes are described, as well as methods for the preparation and pharmaceutical compositions of the same, which are useful in preventing or treating cancer, restenosis, psoriasis, endometriosis, atherosclerosis, or viral infections.

30 Claims, No Drawings

COMBINATIONS OF PROTEIN FARNESYLTRANSFERASE AND HMG COA REDUCTASE INHIBITORS AND THEIR USE TO TREAT CANCER

This application is a 371 of PCT/US99/10188 filed May 10, 1999, which claims benefit of Provisional Serial No. 60/085,202 filed May 12, 1998 and Provisional Application Serial No. 60/092,253 filed Jul. 10, 1998.

FIELD OF THE INVENTION

The present invention relates to combinations of compounds that can be used in the medicinal field to treat, prophylactically or otherwise, uncontrolled or abnormal proliferation of human tissues. Specifically, the present invention relates to the combination of (I) compounds that inhibit protein farnesyltransferase (PFT), which has been determined to activate ras proteins that in turn activate cellular division and are implicated in cancer and restenosis; and (2) compounds that inhibit HMG CoA reductase, a necessary component in the biosynthesis of farnesylpyrophosphate (FPP), which is essential in the activation of ras proteins by PFT.

BACKGROUND OF THE INVENTION

Ras protein (or p21) has been examined extensively because mutant forms are found in 20% of most types of human cancer and greater than 50% of colon and pancreatic carcinomas (Gibbs J. B., *Cells* 1991;65: 1, Cartwright T., et al., *Chimica Oggi.*, 1992; 10:26). These mutant ras proteins are deficient in the capability for feedback regulation that is present in native ras, and this deficiency is associated with their oncogenic action since the ability to stimulate normal cell division cannot be controlled by the normal endogenous regulatory cofactors. The recent discovery that the transforming activity of mutant ras is critically dependent on post-translational modifications (Gibbs J., et al., *Microbiol. Rev.*, 1989;53:171) has unveiled an important aspect of ras function and identified novel prospects for cancer therapy.

In addition to cancer, there are other conditions of uncontrolled cellular proliferation that may be related to excessive expression and/or function of native ras proteins. Post-surgical vascular restenosis is such a condition. The use of various surgical revascularization techniques such as saphenous vein bypass grafting, endarterectomy, and transluminal coronary angioplasty are often accompanied by complications due to uncontrolled growth of neointimal tissue, known as restenosis. The biochemical causes of restenosis are poorly understood and numerous growth factors and protooncogenes have been implicated (Naftilan A. J., et al., *Hypertension*, 1989; 13:706 and *J. Clin. Invest.*, 83:1419; Gibbons G. H., et al., *Hypertension*, 1989;14:358; Satoh T., et al., *Molec. Cell. Biol.*, 1993;13:3706). The fact that ras proteins are known to be involved in cell division processes makes them a candidate for intervention in many situations where cells are dividing uncontrollably. In direct analogy to the inhibition of mutant ras related cancer, blockade of ras dependant processes has the potential to reduce or eliminate the inappropriate tissue proliferation associated with restenosis, particularly in those instances where normal ras expression and/or function is exaggerated by growth stimulatory factors.

Ras functioning is dependent upon the modification of the proteins in order to associate with the inner face of plasma membranes. Unlike other membrane-associated proteins, ras proteins lack conventional transmembrane or hydrophobic sequences and are initially synthesized in a cytosol soluble form. Ras protein membrane association is triggered by a series of post-translational processing steps that are signaled by a carboxyl terminal amino acid consensus sequence that is recognized by protein farnesyltransferase (PFT). This consensus sequence consists of a cysteine residue located four amino acids from the carboxyl terminus, followed by two lipophilic amino acids, and the C-terminal residue. The sulfhydryl group of the cysteine residue is alkylated by farnesylpyrophasphate (FPP) in a reaction that is catalyzed by PFT. Following prenylation, the C-terminal three amino acids are cleaved by an endoprotease and the newly exposed alpha-carboxyl group of the prenylated cysteine is methylated by a methyl transferase. The enzymatic processing of ras proteins that begins with farnesylation enables the protein to associate with the cell membrane. Mutational analysis of oncogenic ras proteins indicate that these post-translational modifications are essential for transforming activity. Replacement of the consensus sequence cysteine residue with other amino acids gives a ras protein that is no longer farnesylated, fails to migrate to the cell membrane and lacks the ability to stimulate cell proliferation (Hancock J. F., et al., *Cell*, 1989;57:1617, Schafer W. R., et al., *Science*, 1989;245:379, Casey P. J., *Proc. Natl. Acad. Sci. USA*, 1989;86:8323).

Recently, PFTs have been identified and a specific PFT from rat brain was purified to homogeneity (Reiss Y., et al., *Bioch. Soc. Trans.*, 1992;20:487–88). The enzyme was characterized as a heterodimer composed of one alpha-subunit (49 kDa) and one beta-subunit (46 kDa), both of which are required for catalytic activity. High level expression of mammalian PFT in a baculovirus system and purification of the recombinant enzyme in active form has also been accomplished (Chen W.-J., et al., *J. Biol. Chem.*, 1993;268:9675).

In light of the foregoing, the discovery that the function of oncogenic ras proteins is critically dependent on their post-translational processing provides a means of cancer chemotherapy through inhibition of the processing enzymes. The identification and isolation of a PFT that catalyzes the addition of a farnesyl group to ras proteins provides a promising target for such intervention. Ras farnesyltransferase inhibitors have been shown to have anticancer activity in several recent articles.

Ras inhibitor agents act by inhibiting farnesyltransferase, the enzyme that anchors the protein product of the ras gene to the cell membrane. The role of the ras mutation in transducing growth signals within cancer cells relies on the protein being in the cell membrane so with farnesyltransferase inhibited, the ras protein will stay in the cytosol and be unable to transmit growth signals: these facts are well-known in the literature.

A peptidomimetic inhibitor of farnesyltransferase B956 and its methyl ester B 1086 at 100 mg/kg have been shown to inhibit tumor growth by EJ-1 human bladder carcinoma, HT1080 human fibrosarcoma and human colon carcinoma xenografts in nude mice (Nagasu, T., et al., *Cancer Res.*, 1995;55:5310–5314). Furthermore, inhibition of tumor growth by B956 has been shown to correlate with inhibition of ras post-translational processing in the tumor. Other ras farnesyltransferase inhibitors have been shown to specifically prevent ras processing and membrane localization and are effective in reversing the transformed phenotype of mutant ras containing cells (Sepp-Lorenzino L., et al., *Cancer Res.*, 1995;55:5302–5309).

In another report (Sun J., et al., *Cancer Res.*, 1995;55:4243–4247), a ras farnesyltransferase inhibitor FT1276 has been shown to selectively block tumor growth in nude mice of a human lung carcinoma with K-ras mutation and p53 deletion. In yet another report, daily administration of a ras farnesyltransferase inhibitor L-744,832 caused tumor regression of mammary and salivary carcinomas in ras transgenic mice (Kohl, et al., *Nature Med.*, 1995;1(8):792–748). Thus, ras farnesyltransferase inhibitors have benefit in certain forms of cancer, including those dependent on oncogenic ras for their growth. However, it is well-known that human cancer is often manifested when several mutations in important genes occurs, one or more of which may be responsible for controlling growth and metastases. A single mutation may not be enough to sustain growth and only after two of three mutations occur, tumors can develop and grow. It is therefore difficult to determine which of these mutations may be primarily driving the growth in a particular type of cancer. Thus, ras farnesyltransferase inhibitors can have therapeutic utility in tumors not solely dependent on oncogenic forms of ras for their growth. For example, it has been shown that various ras farnesyltransferase inhibitors have antiproliferative effects in vivo against tumor lines with either wild-type or mutant ras (Sepp-Lorenzino, supra, 1995). In addition, there are several ras-related proteins that are prenylated. Proteins such as R-Ras2/TC21 are ras-related proteins that are prenylated in vivo by both farnesyltransferase and geranylgeranyl transferase I (Carboni, et al., *Oncogene*, 1995;10:1905–1913). Therefore, ras farnesyltransferase inhibitors could also block the prenylation of the above proteins and therefore would then be useful in inhibiting the growth of tumors driven by other oncogenes.

With regard to the restenosis and vascular proliferative diseases, it has been shown that inhibition of cellular ras prevents smooth muscle proliferation after vascular injury in vivo (Indolfi C, et al., *Nature Med.*, 1995; 1 (6):541–545). This report definitively supports a role for farnesyltransferase inhibitors in this disease, showing inhibition of accumulation and proliferation of vascular smooth muscle.

Inhibitors of the enzyme 3-hydroxy-3methylglutaryl-coenzyme A reductase or HMG CoA reductase (the major regulatory enzyme of the mevalonate pathway of cholesterol synthesis) have also been shown to display anticancer activity in experimental models. In one study, it was shown that inhibition of HMG CoA reductase by lovastatin selectively inhibited tumor growth in vitro and in animal models of hepatocellular, pancreatic, and central nervous system tumors (Maltese, et al., *J. Clin. Invest.*, 1985;76:1748–1754). It has been observed that neoplastic cells synthesize large quantities of cholesterol from precursors such as mevalonate, which is also the precursor of isoprenoid moieties that are incorporated into or linked to several molecules essential for cell growth and replication. More specifically, these drugs inhibit HMG CoA reductase, the rate limiting enzyme for the production of polyisoprenoids and the farnesyl pyrophosphate precursor.

In light of the foregoing, the discovery that HMG CoA reductase inhibitors are important factors in cell growth and replication provides a means of cancer chemotherapy through inhibition of this enzyme. The identification and isolation of an HMG CoA reductase inhibitor that promotes uncontrolled cell growth and replication provides a promising target for such intervention.

SUMMARY OF THE INVENTION

The present invention provides novel combinations of (1) compounds that inhibit protein farnesyltransferase (PFT); and (2) compounds that inhibit HMG CoA reductase. In yet another aspect of the present invention, are disclosed pharmaceutical compositions which comprise therapeutically effective amounts of the novel combinations and a pharmaceutically acceptable carrier. In yet a further aspect of the present invention, are disclosed methods of using the pharmaceutical compositions to treat cancer, restenosis, psoriasis, proliferative cardiovascular disorders and the like.

In one embodiment, the compounds that inhibit PFT are preferably those that have an inhibitory action on PFT in an FPP-competitive nature and/or are cell permeable.

In another embodiment, the compounds that have an inhibitory action on PFT are those compounds having the Formula I

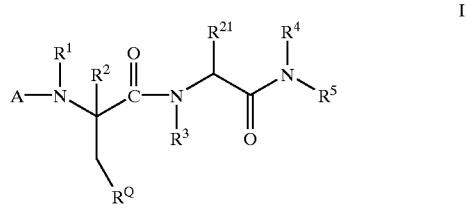

wherein
$R^{21}$ is hydrogen or $C_1$–$C_6$ alkyl;
$R^Q$ is

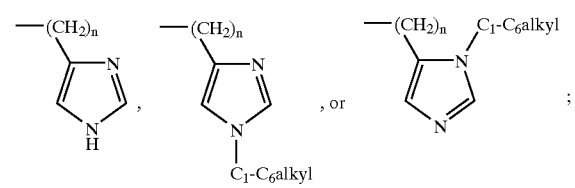

n is 0 or 1;

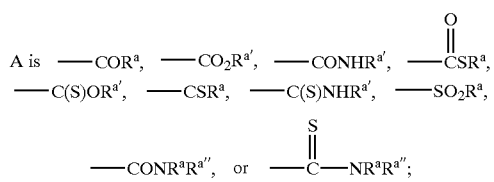

$R^a$, $R^{a'}$, and $R^{a'''}$ are independently $C_1$–$C_6$ alkyl, —$(CH_2)_m$-cycloalkyl, —$(CH_2)_m$-aryl, or —$(CH_2)_m$-heteroaryl;
each m is independently 0 to 3;
$R^1$, $R^2$, and $R^4$ are independently hydrogen or $C_1$–$C_6$ alkyl;

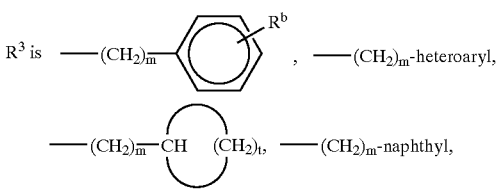

—$(CH_2)_m$-(heteroaryl substituted with $R^b$), or $C_1$–$C_6$ alkyl;
t is 2 to 6;

$R^b$ is —O-phenyl, —O-benzyl, halogen, $C_1$–$C_6$ alkyl, hydrogen, —O—$C_1$–$C_6$ alkyl, —$NH_2$, —$NHR^a$, $NR^aR^{a'}$,

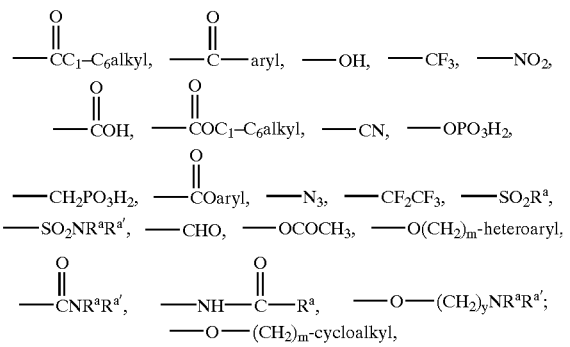

—$(CH_2)_m$-cycloalkyl, —O—$(CH_2)_m$-aryl, —$(CH_2)_m$-aryl, or —$(CH_2)_m$-heteroaryl;
y is 2 or 3;
$R^5$ is

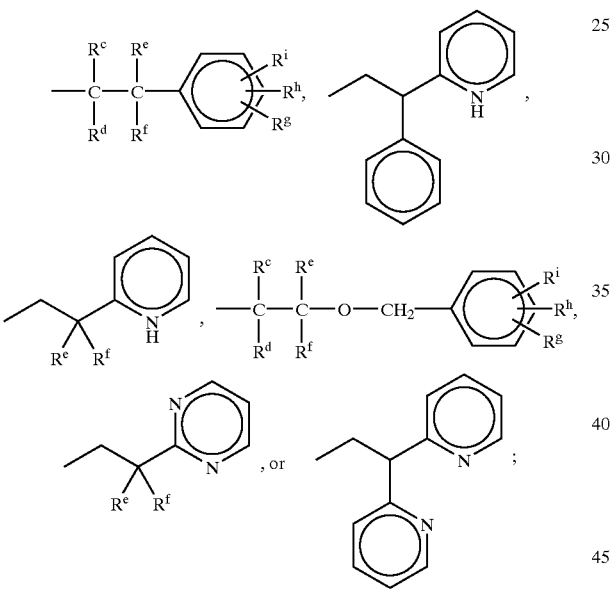

$R^i$, $R^g$, and $R^h$ are independently hydrogen, halogen, —$OC_1$–$C_6$ alkyl, $C_1$–$C_6$ alkyl,

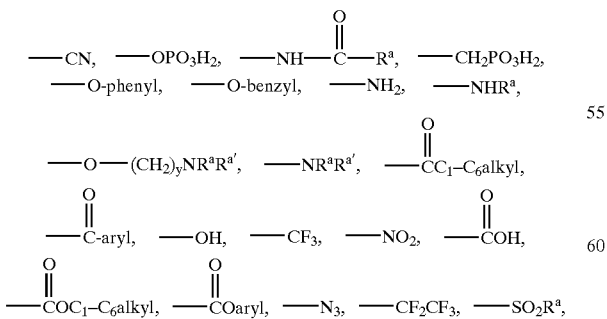

—$SO_2NR^aR^{a'}$, —CHO, or —$OCOCH_3$; and
$R^c$, $R^d$, $R^e$, and $R^f$ are independently $C_1$–$C_6$ alkyl, —$(CH_2)_m$-phenyl, hydrogen, —$(CH_2)_m$—OH, —$(CH_2)_mNH_2$, —$(CH_2)_m$-cycloalkyl, or —CN, and the pharmaceutically acceptable salts, esters, amides, and prodrugs thereof.

In a preferred embodiment of the compounds of Formula I $R^1$ is hydrogen, $R^2$ is hydrogen, $R^4$ is hydrogen, $R^{21}$ is hydrogen or $CH_3$; and A is

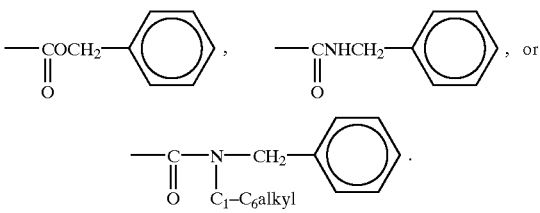

In another preferred embodiment of the compound of Formula I $R^3$ is

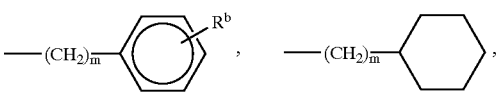

or —$CH_2$—$CH(CH_3)_2$.

$R^1$ is hydrogen, $R^2$ is hydrogen, $R^4$ is hydrogen, and $R^{21}$ is hydrogen or $CH_3$.

In another preferred embodiment of the compounds of Formula I $R^5$ is

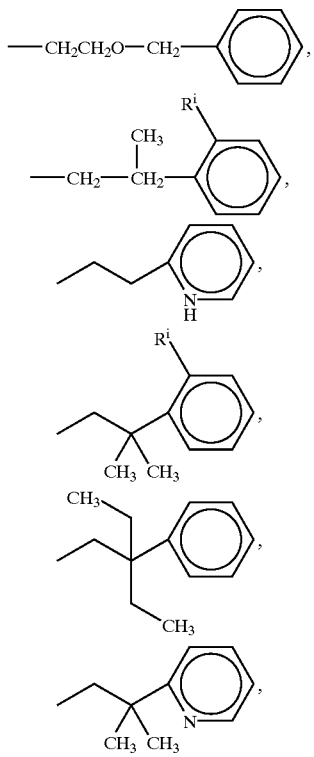

-continued

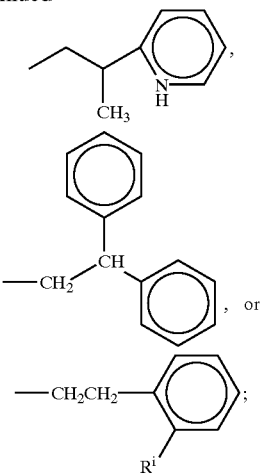

where $R^i$ is hydrogen, Cl, Br, F, or $NH_2$.

Also provided are compounds having the Formula II

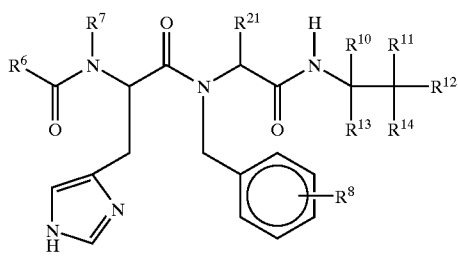

wherein $R^6$ is —O-benzyl, —NH-benzyl, or

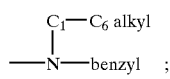

$R^{21}$ is hydrogen or methyl;
$R^7$ is hydrogen or methyl;
$R^8$ is hydrogen, halogen, $C_1$–$C_6$ alkyl, —O-benzyl, —O$C_1$–$C_6$ alkyl, —$CF_3$, —OH, —O—$(CH_2)_m$-pyridyl, or phenyl;
$R^{10}$, $R^{11}$, $R^{13}$, and $R^{14}$ are independently hydrogen, $C_1$–$C_6$ alkyl, or —$(CH_2)_m$-phenyl;
each m is independently 0 to 3;
$R^{12}$ is

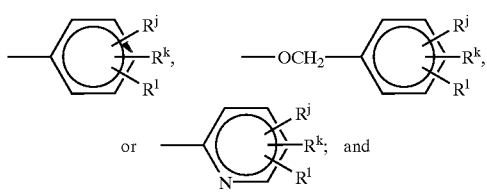

$R^j$, $R^k$, and $R^l$ are independently hydrogen, halogen, —O$C_1$–$C_6$ alkyl, —$C_1$–$C_6$ alkyl, —$NHR^a$, or $NH_2$, and the pharmaceutically acceptable salts, esters, amides, and prodrugs thereof.

In a preferred embodiment of the compounds of Formula II, $R^{11}$ and $R^{14}$ are methyl.

In another preferred embodiment of the compounds of Formula II, $R^8$ is methyl or methoxy.

Also provided are compounds having the Formula III

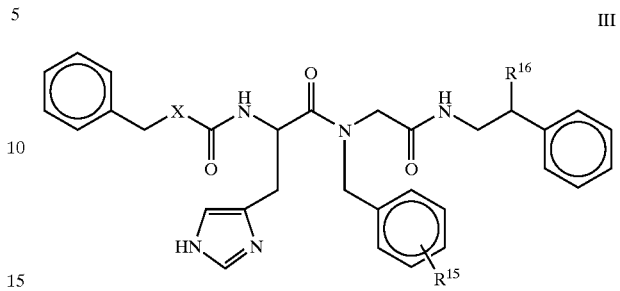

wherein

X is NH, O or —$N(CH_3)$;
$R^{15}$ is —O-benzyl, —$CF_3$, hydrogen, halogen, —O$C_1$–$C_6$ alkyl, phenyl, —O—$(CH_2)_m$-pyridyl, or —$C_1$–$C_6$ alkyl;
m is 0 to 3; and
$R^{16}$ is a phenyl, hydrogen, or $C_1$–$C_6$ alkyl, and the pharmaceutically acceptable salts, esters, amides, and prodrugs thereof.

Also provided are compounds having the Formula IV

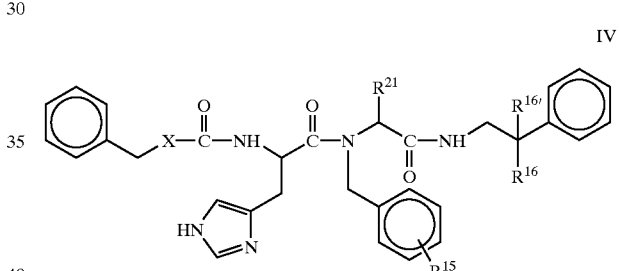

wherein

X is NH, O or $N(CH_3)$;
$R^{15}$ is —O-benzyl, —$CF_3$, hydrogen, halogen, $C_1$–$C_6$ alkyl, —O—$C_1$–$C_6$ alkyl, phenyl, or —O—$(CH_2)_m$-pyridyl;
$R^{16}$ and $R^{16'}$ are $C_1$–$C_6$ alkyl;
m is 0 to 3; and
$R^{21}$ is hydrogen or methyl, and the pharmaceutically acceptable salts, esters, amides, and prodrugs thereof.

In another embodiment, the compounds that have an inhibitory action on PFT are those compounds having the Formula V

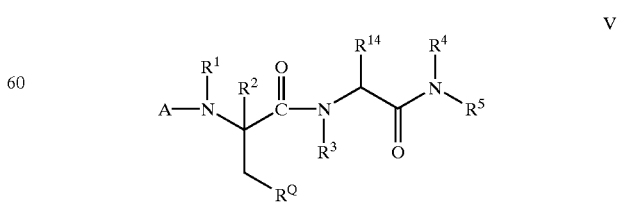

wherein $R^Q$ is

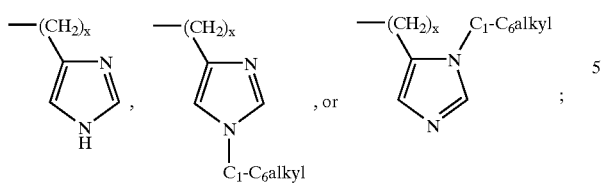

$R^5$ is

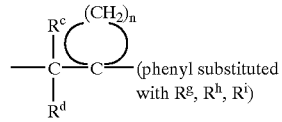

or

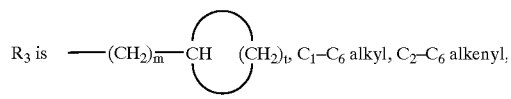

X is 0 or 1;

$R^{14}$ is hydrogen or $C_1$–$C_6$ alkyl;

A is —$COR^a$, —$CO_2R^{a\prime}$, —$CONHR^{a\prime}$, —$CSR^a$,

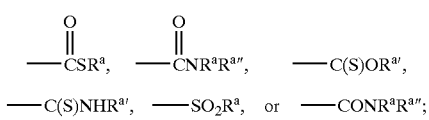

$R^a$, $R^{a\prime}$, and $R^{a\prime\prime\prime}$ are independently $C_1$–$C_6$ alkyl, —$(CH_2)_m$-cycloalkyl, —$(CH_2)_m$-aryl, or —$(CH_2)_m$-heteroaryl;

each m is independently 0 to 3;

$R^1$, $R^2$, and $R^4$ are independently hydrogen or $C_1$–$C_6$ alkyl;

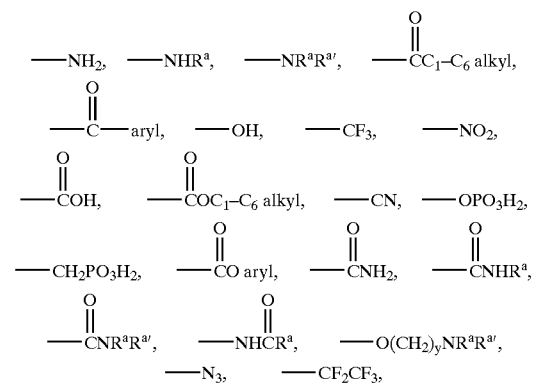

—$(CH_2)_m$-heteroaryl, —$(CH_2)_m$-naphthyl, —$(CH_2)_m$-(phenyl substituted with $R^b$), or —$(CH_2)_m$-(heteroaryl substituted with $R^b$);

t is 2 to 6;

$R^b$ is —O-phenyl, —O-benzyl, halogen, $C_1$–$C_6$ alkyl, hydrogen, —$OC_1$–$C_6$ alkyl, —$NH_2$, —$NHR^a$, —$NR^aR^{a\prime}$, —$\overset{O}{\overset{\|}{C}}C_1$–$C_6$ alkyl,
—$\overset{O}{\overset{\|}{C}}$—aryl, —OH, —$CF_3$, —$NO_2$,
—COH, —$\overset{O}{\overset{\|}{C}}OC_1$–$C_6$ alkyl, —CN, —$OPO_3H_2$,
—$CH_2PO_3H_2$, —$\overset{O}{\overset{\|}{C}}O$ aryl, —$\overset{O}{\overset{\|}{C}}NH_2$, —$\overset{O}{\overset{\|}{C}}NHR^a$,
—$\overset{O}{\overset{\|}{C}}NR^aR^{a\prime}$, —$NHCR^a$, —$O(CH_2)_yNR^aR^{a\prime}$,
—$N_3$, —$CF_2CF_3$, —$SO_2R^a$, —$SO_2NR^aR^{a\prime}$, —CHO, —$OCOCH_3$, —$O(CH_2)_m$-heteroaryl, —$O(CH_2)_m$-aryl, —$O(CH_2)_m$-cycloalkyl, —$(CH_2)_m$-aryl, —$(CH_2)_m$-cycloalkyl, —$(CH_2)_m$-heteroaryl, or —CH=$CHC_6H_5$;

y is 2 or 3;

each n is independently 2, 3, or 4;

$R^i$, $R^g$, and $R^h$ are independently hydrogen, halogen, —$OC_1$–$C_6$ alkyl, $C_1$–$C_6$ alkyl, —CN, —$OPO_3H_2$, —$CH_2PO_3H_2$, —O-phenyl, —O-benzyl, —$NH_2$, —$NHR^a$, —$NHR^aR^{a\prime}$, —$\overset{O}{\overset{\|}{C}}C_1$–$C_6$ alkyl, —$\overset{O}{\overset{\|}{C}}$—aryl,
—$\overset{O}{\overset{\|}{C}}NH_2$, —$\overset{O}{\overset{\|}{C}}NHR^a$, —$\overset{O}{\overset{\|}{C}}NR^aR^{a\prime}$, —$NHCR^a$,
—$O(CH_2)_yNR^aR^{a\prime}$, —OH, —$CF_3$, —$NO_2$,
—$\overset{O}{\overset{\|}{C}}OH$, —$\overset{O}{\overset{\|}{C}}OC_1$–$C_6$ alkyl, —$\overset{O}{\overset{\|}{C}}O$ aryl, —$N_3$,
—$CF_2CF_3$, —$SO_2R^a$, —$SO_2NR^aR^{a\prime}$, —CHO, or —$OCOCH_3$; and $R^c$ and $R^d$ are independently $C_1$–$C_6$ alkyl, —$(CH_2)_m$-cycloalkyl or hydrogen, and the pharmaceutically acceptable salts, esters, amides, and prodrugs thereof.

In another preferred embodiment of the compounds of Formula V $R^1$ is hydrogen, $R^2$ is hydrogen, $R^4$ is hydrogen, $R^{14}$ is hydrogen or methyl, and A is

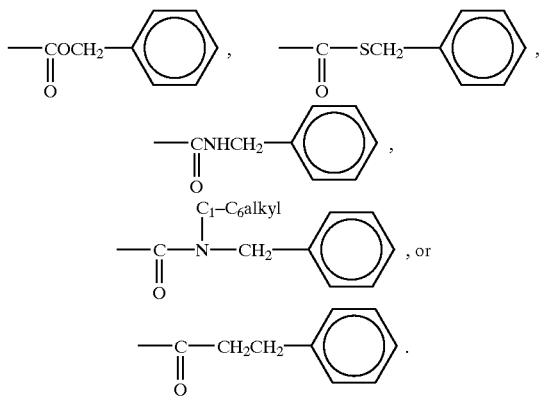

In another preferred embodiment of the compounds of Formula V

R₃ is 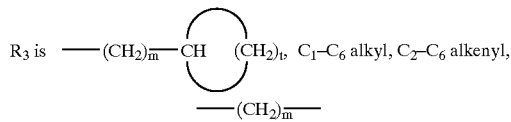 $C_1$–$C_6$ alkyl, $C_2$–$C_6$ alkenyl, (phenyl substituted with $R^b$), or —$(CH_2)_m$-(heteroaryl substituted with $R^b$).

$R^1$ is hydrogen, $R^2$ is hydrogen, $R^4$ is hydrogen, and $R^{14}$ is hydrogen or methyl.

In another preferred embodiment of the compounds of Formula V $R^5$ is

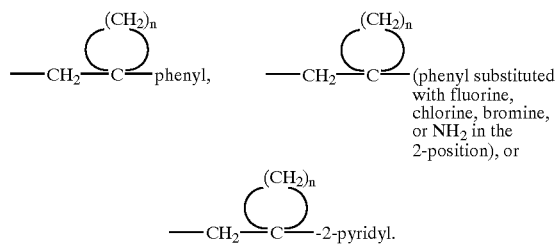

In another embodiment, the compounds that have an inhibitory action on PFT are those compounds having the Formula VI

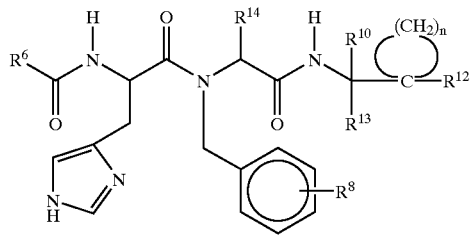

wherein $R^6$ is —O-benzyl, —NH-benzyl, —N($C_1$–$C_6$ alkyl)-benzyl, or —$SCH_2$-phenyl;

$R^8$ is hydrogen, halogen, $C_1$–$C_6$ alkyl, —O-benzyl, —$OCH_2$-pyridyl, —$OC_1$–$C_6$ alkyl, —$CF_3$, —OH, or —phenyl;

$R^{10}$ and $R^{13}$ are independently hydrogen or $C_1$–$C_6$ alkyl;

each n is independently 2, 3, or 4;

$R^{14}$ is hydrogen or methyl;

$R^{12}$ is 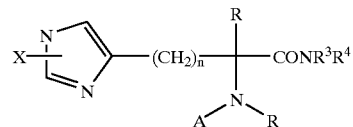

$R^j$, $R^k$, and $R^l$ are independently hydrogen, halogen, —$NH_2$, —$NHR^a$, —$OC_1$–$C_6$ alkyl, or —$C_1$–$C_6$ alkyl, and the pharmaceutically acceptable salts, esters, amides, and prodrugs thereof.

In another embodiment, the compounds that have an inhibitory action on PFT are those compounds having the Formula VII

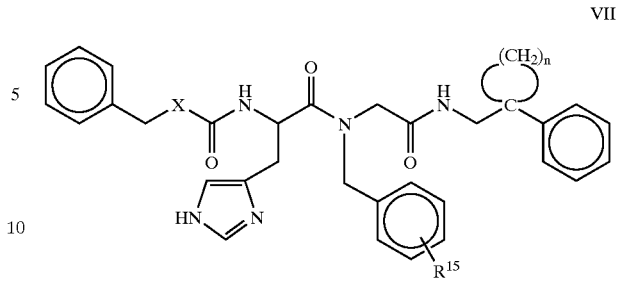

wherein each n is 2, 3, or 4;

X is NH, O or —$NCH_3$;

$R^{15}$ is —O-benzyl, —$CF_3$, hydrogen, halogen, —OH, -phenyl, —$C_1$–$C_6$ alkyl, —$OCH_2$-pyridyl, or —$OC_1$–$C_6$ alkyl, and the pharmaceutically acceptable salts, esters, amides, and prodrugs thereof.

In another embodiment, the compounds that have an inhibitory action on PFT are those compounds having the Formula VIII

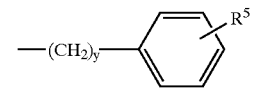

wherein:

n is 1 or 2;

A is $COR^2$, $CO_2R^2$, $CONHR^2$, $CSR^2$, $C(S)OR^2$, $C(S)NHR^2$, or $SO_2R^2$ with $R^2$ as defined below;

R is independently H or Me;

$R^2$ is alkyl, $(CH_2)_m$-cycloalkyl, $(CH_2)_m$-aryl, $(CH_2)_m$-heteroaryl with m is 0, 1, 2, or 3;

$R^3$ and $R^4$ are independently

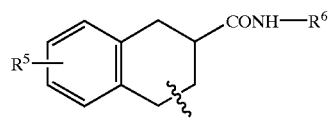

or $(CH_2)_n CONH$—$R^6$ with y is 1–5 and n as defined above and with $R^5$ and $R^6$ as defined below, or $R^3$ and $R^4$ are connected together to form a ring of the following type:

with $R^5$ and $R^6$ as defined below, or $(CH_2)_x$—$R^7$, with x is 2–5, and $R^7$ as defined below;

$R^5$ is $R^2$, $OR^2$, or $SR^2$ with $R^2$ as defined above;

$R^6$ is $(CH_2)_n R^5$, $(CH_2)_n CO_2 R^2$, $(CH_2)_n CONHR^2$, $CH_2)_n CONH(CH_2)_{n+1} R^5$, $CH(COR^8)(CH_2)_n R^5$, with n, $R^2$, and $R^5$ as defined above and $R^8$ as defined below;

$R^7$ is $(CH_2)_m$-cycloalkyl, $(CH_2)_m$-aryl, $(CH_2)_m$-heteroaryl, $O(CH_2)_m$-cycloalkyl, $O(CH_2)_m$-aryl, $O(CH_2)_m$-heteroaryl with m is 0, 1, 2, or 3;

13

$R^8$ is OH, O-alkyl, $NH_2$, or NH-alkyl; and

X is H, Me, $(CH_2)_nCO_2R^9$, or $(CH_2)_nP(O)(OR^9)_2$, with $R^9$ is H or alkyl;

and the pharmaceutically acceptable salts, esters, amides, and prodrugs thereof.

In another embodiment, the compounds that have an inhibitory action on PFT are those compounds having the Formulas IX and X.

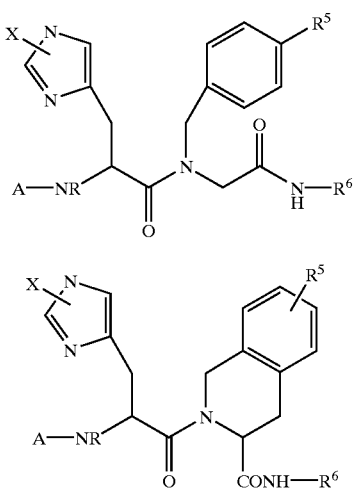

wherein:

A is limited to $CO_2R^2$, $CONHR^2$, $C(S)OR^2$, or $C(S)NHR^2$ with $R^2$ as defined below;

R is H or Me;

$R^2$ is limited to alkyl, $(CH_2)_m$-cycloalkyl, $(CH_2)_m$-aryl, $(CH_2)_m$-heteroaryl, with m is 0, 1, 2, or 3;

$R^5$ is limited to $(CH_2)_m$-aryl, O—$(CH_2)_m$-aryl, or O—$(CH_2)_m$-heteroaryl with m as defined above;

$R^6$ is limited to $CH_2$—$R^5$, $CH_2CO_2R^2$, $CH_2CONHR^2$, with n is 1 or 2, and with $R^5$ and $R^2$ as defined above; and X is limited to H or Me;

and pharmaceutically acceptable salts, esters, amides, and prodrugs thereof.

In a preferred embodiment of the compounds of Formulas IX and X,

A is further limited to $CO_2R^2$ or $CONHR^2$, with $R^2$ as defined below;

R is limited to H;

$R^2$ is further limited to alkyl, or $(CH_2)_m$-aryl with m is 0, 1, 2, or 3;

$R^5$ is further limited to $(CH_2)_m$-aryl or O—$(CH_2)_m$-aryl with m as defined above;

$R^6$ is limited to $CH_2$—$R^5$ or $CH_2CONHR^2$, with n is 1 or 2, and with $R^5$ and $R^2$ as defined above; and X is limited to H or Me.

The compounds of the present invention that are PTE inhibitors, and their method of preparation are disclosed in copending U.S. Ser. Nos. 60/033,662 and 60/056,831, filed Dec. 17, 1996, and Aug. 22, 1997, respectively, and U.S. Pat. No. 5,571,792 issued Nov. 5, 1996. The information contained in these copending cases and patent are incorporated herein by reference.

Compounds that inhibit HMG CoA reductase are known to those of skill in the art. HMG CoA reductase inhibitors of the present invention include, but are not limited to the following compounds: lovastatin, provastatin, atorvastatin, velostatin, simvastatin and the like.

In another aspect, the present invention provides a pharmaceutically acceptable composition that comprises a combination of the compound of Formula I, II, III, IV, V, VI, VII, VIII, IX, and/or X and an HMG CoA reductase inhibitor.

Also provided is a method of treating or preventing restenosis, the method comprising administering to a patient having restenosis or a risk of having restenosis a therapeutically effective amount of a combination of the compound of Formula I, II, III, IV, V, VI, VII, VIII, IX, and/or X and a compound that is an HMG CoA reductase inhibitor.

Also provided is a method of treating cancer, the method comprising administering to a patient having cancer a therapeutically effective amount of a combination of a compound of Formula I, II, III, IV, V, VI, VII, VIII, IX, and/or X and a compound that is an HMG CoA reductase inhibitor.

Also provided is a method of treating psoriasis, the method comprising administering to a patient having psoriasis a therapeutically effective amount of a combination of a compound of Formula I, II, III, IV, V, VI, VII, VIII, IX, and/or X and a compound that is an HMG CoA reductase inhibitor.

Also provided is a method of treating viral infection, the method of comprising administering to a patient having a viral infection a therapeutically effective amount of a combination of a compound of Formula I, II, III, IV, V, VI, VII, VIII, IX, and/or X and a compound which is an HMG CoA reductase inhibitor.

In a more preferred embodiment, the cancer is lung cancer, colon cancer, breast cancer, pancreatic cancer, thyroid cancer, or bladder cancer.

In a most preferred embodiment, the compounds of Formula I, II, III, IV, V, VI, VII, VIII, IX, and X are (S)-[1-[(4-Benzyloxy-benzyl)-(phenethyl-carbamoyl-methyl)-carbamoyl]-2-(3H-imidazole-4-yl)-ethyl]-carbamic acid benzyl ester;

(S)-[1-[[2-Benzyloxy-ethylcarbamoyl]-methyl]-[4-chlorobenzyl]-carbamoyl]-2-(1H-imidazole-4-yl)-ethyl]-carbamic acid benzyl ester;

(S)-[1-[(4-Benzyloxy-benzyl)-[(2-phenyl-propyl-carbamoyl)-methyl]-carbamoyl]-2-(1H-imidazole-4-yl)-ethyl]carbamic acid benzyl ester;

(S)-[1-[(4-Benzyloxy-benzyl)-[(2,2-diphenyl-ethylcarbamoyl)-methyl]-carbamoyl]-2-(1H-imidazole-4-yl)-ethyl]-carbamic acid benzyl ester;

(S)-N-(4-Benzyloxy-benzyl)-2-(3-benzyl-ureido)-3-(1H-imidazole4yl)-N-[(2-phenyl-propylcarbamoyl)-methyl]-propionamide;

(S)-[1-{Biphenyl-4-ylmethyl-[(2-methyl-2-phenyl-propylcarbamoyl)-methyl]-carbamoyl}-2-(1H-imidazole-4-yl)-ethyl]-carbamic acid benzyl ester;

(S)-[1-{Biphenyl-4-ylmethyl-[(2-phenyl-propylcarbamoyl)-methyl]-carbamoyl}-2-(1H-imidazole-4-yl)-ethyl]-carbamic acid benzyl ester;

(S)-[1-((4-Benzyloxy-benzyl)-{[2-(2-fluoro-phenyl)-ethylcarbamoyl]-methyl}-carbamoyl)-2-(1H-imidazole-4-yl)-ethyl]-carbamic acid benzyl ester;

(S)-[1-{(4-Benzyloxy-benzyl)-[(2-pyridin-2-yl-ethylcarbamoyl)-methyl]-carbamoyl}-2-(1H-imidazole-4-yl)-ethyl]-carbamic acid benzyl ester;

(S)-[1-((4-Benzyloxy-benzyl)-{[2-(2-bromo-phenyl)-ethylcarbamoyl]-methyl}-carbamoyl)-2-(1H-imidazole-4-yl)-ethyl]-carbamic acid benzyl ester;

(S)-[1-{(4-Benzyloxy-benzyl)-[(1-methyl-2-phenyl-ethylcarbamoyl)-methyl]-carbamoyl}-2-(1H-imidazole-4-yl)-ethyl]-carbamic acid benzyl ester;

(S)-[1-{(4-Benzyloxy-benzyl)-[(2-phenyl-2-pyridin-2-yl-ethylcarbamoyl)-methyl]-carbamoyl}-2-(1H-imidazole-4-yl)-ethyl]-carbamic acid benzyl ester;

(S)-[1-{(4-Chloro-benzyl)-[(2-phenyl-propylcarbamoyl)-methyl]-carbamoyl}-2-(1H-imidazole-4-yl)-ethyl]-carbamic acid benzyl ester;

(S)-[1-{(4-Benzyloxy-benzyl)-[(2-phenyl-butylcarbamoyl)-methyl]-carbamoyl}-2-(1H-imidazole-4-yl)-ethyl]-carbamic acid benzyl ester;

(S)-N-(4-Benzyloxy-benzyl)-3-(1H-imidazole-4-yl)-2-(3-phenyl-propionylamino)-N-[(2-phenyl-propylcarbamoyl)-methyl]-propionamide;

(S)-[1-{(4-Fluoro-benzyl)-[(2-phenyl-propylcarbamoyl)-methyl]-carbamoyl}-2-(1H-imidazole-4-yl)-ethyl]-carbamic acid benzyl ester;

(S)-(2-(1H-Imidazole-4-yl)-1-{(4-methyl-benzyl)-[(2-phenyl-propylcarbamoyl)-methyl]-carbamoyl}-ethyl)-carbamic acid benzyl ester;

(S)-(2-(1H-Imidazole-4-yl)-1-{(4-methoxy-benzyl)-[(2-phenyl-propylcarbamoyl)-methyl]-carbamoyl}-ethyl)-carbamic acid benzyl ester;

(S)-[1-[{[2-(2-Amino-phenyl)-propylcarbamoyl]-methyl}-(4-benzyloxy-benzyl)-carbamoyl]-2-(3H-imidazole-4-yl)-ethyl]-carbamic acid benzyl ester;

(S)-[1-{(4-Fluoro-benzyl)-[(2-methyl-2-phenyl-propylcarbamoyl)-methyl]-carbamoyl}-2-(1H-imidazole-4-yl)-ethyl]-carbamic acid benzyl ester;

(S)-[1-{Benzyl-[(2-phenyl-propylcarbamoyl)-methyl]-carbamoyl}-2-(1H-imidazole-4-yl)-ethyl]-carbamic acid benzyl ester;

(S)-[1-((4-Benzyloxy-benzyl)-{[2-(2-chloro-phenyl)-2-phenyl-ethylcarbamoyl]-methyl}-carbamoyl)-2-(1H-imidazole-4-yl)-ethyl]-carbamic acid benzyl ester;

(S)-[1-{(4-Benzyloxy-benzyl)-[(2-ethyl-2-phenyl-butylcarbamoyl)-methyl]-carbamoyl}-2-(3H-imidazole-4-yl)-ethyl]-carbamic acid benzyl ester;

(S)-N-(4-Benzyloxy-benzyl)-2-(3-benzyl-ureido)-3-(1H-imidazole-4-yl)-N-[(2-phenyl-propylcarbamoyl)-methyl]-propionamide;

(S)-N-(4-Benzyloxy-benzyl)-2-(3-benzyl-ureido)-3-(1H-imidazole4-yl)-N-[(2-phenyl-butylcarbamoyl)-methyl]-propionamide;

(S)-1-{(2-Chloro-benzyl)-[(2-phenyl-propylcarbamoyl)-methyl]-carbamoyl}-2-(1H-imidazole-4-yl)-ethyl]-carbamic acid benzyl ester;

(S)-[1-{(4-Bromo-benzyl)-[(2-phenyl-propylcarbamoyl)-methyl]-carbamoyl}-2-(1H-imidazole-4-yl)-ethyl]-carbamic acid benzyl ester;

(S)-[1-{(3-Chloro-benzyl)-[(2-phenyl-propylcarbamoyl)-methyl)]-carbamoyl}-2-(1H-imidazole-4-yl)-ethyl]-carbamic acid benzyl ester;

(S)-[1-{(4-Chloro-benzyl)-[(2-methyl-2-phenyl-propylcarbamoyl)-methyl-}-carbamoyl}-2-(1H-imidazole-4-yl)-ethyl]-carbamic acid benzyl ester;

(S)-[1-((4-Benzyloxy-benzyl)-{[2-(2-chloro-phenyl)-propylcarbamoyl]-methyl}-carbamoyl)-2-(1H-imidazole-4-yl)-ethyl]-carbamic acid benzyl ester;

(S)-(2-(1H-Imidazole-4-yl)-1-{(2-methoxy-benzyl)-[(2-phenyl-propylcarbamoyl)-methyl]-carbamoyl}-ethyl)-carbamic acid benzyl ester;

(S)-(2-(1H-Imidazole-4-yl)-1-{[(2-phenyl-propylcarbamoyl)-methyl]-[4-(pyridin-4-ylmethoxy)-benzyl]-carbamoyl}-ethyl)-carbamic acid benzyl ester;

(S)-(2-(1H-Imidazole-4-yl)-1-{(3-methoxy-benzyl)-[(2-phenyl-propylcarbamoyl)-methyl]-carbamoyl}-ethyl)-carbamic acid benzyl ester;

(S)-(2-(1H-Imidazole-4-yl)-1-{[(2-phenyl-propylcarbamoyl)-methyl]-[4-(pyridin-3-ylmethoxy)-benzyl]-carbamoyl}-ethyl)-carbamic acid benzyl ester;

(S)-(2-(1H-Imidazole-4-yl)-1-{naphthalen-1-ylmethyl-[(2-phenyl-propylcarbamoyl)-methyl]-carbamoyl}-ethyl)-carbamic acid benzyl ester;

(S)-{2-(1H-Imidazole-4-yl)-1-[[(2-phenyl-propylcarbamoyl)-methyl]-(4-trifluoromethyl-benzyl)-carbamoyl]-ethyl}-carbamic acid benzyl ester;

(S)-(2-(1H-Imidazole-4-yl)-1-{[(2-methyl-2-phenyl-propylcarbamoyl)-methyl]-pyridin-3-ylmethyl-carbamoyl}-ethyl)-carbamic acid benzyl ester;

(S)-(2-(1H-Imidazole-4-yl)-1-{[(2-methyl-2-phenyl-propylcarbamoyl)-methyl]-[4-(pyridin-2-ylmethoxy)-benzyl]-carbamoyl}-ethyl)-carbamic acid benzyl ester;

(S)-[1-{Benzyl-[(2-methyl-2-phenyl-propylcarbamoyl)-methyl]-carbamoyl}-2-(1H-imidazole-4-yl)-ethyl]-carbamic acid benzyl ester;

(S)-(2-(1H-Imidazole-4-yl)-1-{(2-methyl-benzyl)-[(2-phenyl-propylcarbamoyl)-methyl]-carbamoyl}-ethyl)-carbamic acid benzyl ester;

(S)-(2-(1H-Imidazole-4-yl)-1-{(4-methoxy-benzyl)-[(2-methyl-2-phenyl-propylcarbamoyl)-methyl]-carbamoyl}-ethyl)-carbamic acid benzyl ester;

(S)-[-{(4-Benzyloxy-benzyl)-[(2-cyano-2-phenyl-ethylcarbamoyl)-methyl]-carbamoyl}-2-(1H-imidazole-4-yl)-ethyl]-carbamic acid benzyl ester;

(S)-(2-(1H-Imidazole-4-yl)-1-{[(2-methyl-2-phenyl-propylcarbamoyl)-methyl]-pyridin-2-ylmethyl-carbamoyl}-ethyl)-carbamic acid benzyl ester;

(S)-(2-(1H-Imidazole-4-yl)-1-{(3-methyl-benzyl)-[(2-phenyl-propylcarbamoyl)-methyl]-carbamoyl}-ethyl)-carbamic acid benzyl ester;

(S)-[1-{(4-Dimethylamino-benzyl)-[(2-phenyl-propylcarbamoyl)-methyl]-carbamoyl}-2-(1H-imidazole-4-yl)-ethyl]-carbamic acid benzyl ester;

(S)-(2-(1H-Imidazole-4-yl)-1-{[(2-methyl-2-phenyl-propylcarbamoyl)-methyl]-[4-(pyridin-4-ylmethoxy)-benzyl]-carbamoyl}-ethyl)-carbamic acid benzyl ester;

(S)-(2-(1H-Imidazole-4-yl)-1-{[(2-methyl-2-phenyl-propylcarbamoyl)-methyl]-[4-(pyridin-3-ylmethoxy)-benzyl]-carbamoyl}-ethyl)-carbamic acid benzyl ester;

(2-(1-H-imidazole-4-yl)-1-{isobutyl-[(2-phenyl-propylcarbamoyl)-methyl]-carbamoyl}-ethyl)-carbamic acid benzyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid benzyl ester;

(S)-2-(3-Benzyl-3-methyl-ureido)-N-(4-benzyloxy-benzyl)-3-(1H-imidazole-4-yl)-N-[(2-methyl-2-phenyl-propylcarbamoyl)-methyl]-propionamide;

(S)-[1-{(4-Benzyloxy-benzyl)-[(2-hydroxy-2-phenyl-ethylcarbamoyl)-methyl]-carbamoyl}-2-(3H-imidazole-4-yl)-ethyl]-carbamic acid benzyl ester;

(S)-(2-(1H-Imidazole-4-yl)-1-{(4-methoxy-benzyl)-[(2-phenyl-propylcarbamoyl)-methyl]-carbamoyl}-ethyl)-carbamic acid benzyl ester;

(S)-[1-((4-Benzyloxy-benzyl)-{[2-(2-chloro-phenyl)-ethylcarbamoyl]-methyl}-carbamoyl)-2-(1H-imidazole-4-yl)-ethyl]-carbamic acid benzyl ester;

(S)-[1-{(4-Benzyloxy-benzyl)-[(2-methyl-2-phenyl-propylcarbamoyl)-methyl]-carbamoyl}-2-(1H-imidazole-4-yl)-ethyl]-carbamic acid thiophen-3-ylmethyl ester;

(S)-[1-{(4-Chloro-benzyl)-[1-(2-methyl-2-phenyl-ethyl)-ethylcarbamoyl]-carbamoyl}-2-(3H-imidazole-4-yl)-ethyl]-carbamic acid benzyl ester;

(S)-(2-(1H-Imidazole-4-yl)-1-{(4-methyl-benzyl)-[(2-methyl-2-phenyl-propylcarbamoyl)-methyl]-carbamoyl}-ethyl)-carbamic acid benzyl ester;

(S)-(2-(1H-Imidazole-4-yl)-1-{(2-methoxy-benzyl)-[(2-methyl-2-phenyl-propylcarbamoyl)-methyl]-carbamoyl}-ethyl)-carbamic acid benzyl ester;

(S)-2-(3-Benzyl-3-methyl-ureido)-N-(4-chloro-benzyl)-3-(1H-imidazole-4-yl)-N-[(2-methyl-2-phenyl-propylcarbamoyl)-methyl]-propionamide;

(S)-(2-(1H-Imidazole-4-yl)-1-{(3-methoxy-benzyl)-[(2-methyl-2-phenyl-propylcarbamoyl)-methyl]-carbamoyl}-ethyl)-carbamic acid benzyl ester;

(S)-(2-(1H-Imidazole-4-yl)-1-{[(2-methyl-2-phenyl-propylcarbamoyl)-methyl]-[2-(pyridin-4-ylmethoxy)-benzyl]-carbamoyl}-ethyl)-carbamic acid benzyl ester;

(S)-[1-{Cyclohexylmethyl-[(2-phenyl-propylcarbamoyl)-methyl]-carbamoyl}-2-(3H-imidazole-4-yl)-ethyl]-carbamic acid benzyl ester;

(S)-[1-{(4-Benzyloxy-benzyl)-[(2-phenyl-pentylcarbamoyl)-methyl]-carbamoyl}-2-(3H-Imidazole-4-yl)-ethyl]-carbamic acid benzyl ester;

(S)-[1-{[2-(4-Benzyloxy-phenyl)-ethyl]-[(2-methyl-2-phenyl-propylcarbamoyl)-methyl]-carbamoyl}-2-(3H-imidazole-4-yl)-ethyl]-carbamic acid benzyl ester;

(S)-(2-(3H-imidazole-4-yl)-1-{[2-(4-methoxy-phenyl)-ethyl]-[(2-methyl-2-phenyl-propylcarbamoyl)-methyl]-carbamoyl}-ethyl)-carbamic acid benzyl ester;

(S)-[1-[{[2-(2-Amino-phenyl)-ethylcarbamoyl]-methyl}-(4-benzyloxy-benzyl)-carbamoyl]-2-(3H-imidazole-4-yl)-ethyl]-carbamic acid benzyl ester;

(2-(1H-imidazol-4-yl)-1-{isobutyl-[(2-phenyl-propylcarbamoyl)-methyl]-carbamoyl}-ethyl)-carbamic acid benzyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-methyl-carbamic acid benzyl ester;

(S)-[1-{(4-Benzyloxy-benzyl)-[(2-methyl-2-phenyl-propylcarbamoyl)-methyl]-carbamoyl}-2-(3-methyl-3H-imidazole-4-yl)-ethyl]-carbamic acid benzyl ester;

(S)-[1-{(4-Benzyloxy-benzyl)-[(2-methyl-2-phenyl-propylcarbamoyl)-methyl]-carbamoyl}-2-(1-methyl-1H-imidazole-4-yl)-ethyl]-carbamic acid benzyl ester;

(S)-1-{(4-Benzyloxy-benzyl)-[(2-methyl-2-phenyl-propylcarbamoyl)-methyl]-carbamoyl}-2-(3H-imidazole-4-yl)-ethyl]-carbamic acid furan-2-ylmethyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid thiophen-2-ylmethyl ester;

(S)-1-{(4-Benzyloxy-benzyl)-[(2-methyl-2-phenyl-propylcarbamoyl)-methyl]-carbamoyl}-2-(3H-imidazole-4-yl)-ethyl]-carbamic acid pyridin-3-ylmethyl ester;

(S)-1-{(4-Benzyloxy-benzyl)-[(2-methyl-2-phenyl-propylcarbamoyl)-methyl]-carbamoyl}-2-(3H-imidazole-4-yl)-ethyl]-carbamic acid1H-imidazole-4-ylmethyl ester;

(S)-2-(3-Benzyl-ureido)-N-(4-chloro-benzyl)-3-(3H-imidazole-4-yl)-N-[(2-methyl-2-phenyl-propylcarbamoyl)-methyl]-propionamide;

(S)-[1- ((4-Benzyloxy-benzyl)-[(2-methyl-2-phenyl-propylcarbamoyl)-methyl]-carbamoyl]-2-(3H-imidazole-4-yl)-ethyl]-carbamic acid4-methoxy-benzyl ester;

(S)-2-(3-Benzyl-thioureido)-3-(3H-imidazole-4-yl)-N-(4-methyl-benzyl)-N-[(2-methyl-2-phenyl-propylcarbamoyl)-methyl]-propionamide;

(S)-2-Acetylamino-N-(4-benzyloxy-benzyl)-3-(3H-imidazole-4-yl)-N-[(2-methyl-2-phenyl-propylcarbamoyl)-methyl]-propionamide;

(S)-(2-(3H-imidazole-4-yl)1-{[(2-methyl-2-phenyl-propylcarbamoyl)-methyl]-pyridin-4-ylmethyl-carbamoyl}-ethyl)-carbamic acid benzyl ester;

(S)-{2-(3H-Imidazole-4-yl)1-[(4-iodo-benzyl)-(phenethylcarbamoyl-methyl)-carbamoyl]-ethyl}-carbamic acid benzyl ester;

(S)-1-{(4-Amino-benzyl)-[(2-methyl-2-phenyl-propylcarbamoyl)-methyl]-carbamoyl}-2-(3H-imidazole-4-yl)-ethyl]-carbamic acid benzyl ester;

(S)-1-{(4-Ethoxy-benzyl)-[(2-methyl-2-phenyl-propylcarbamoyl)-methyl]-carbamoyl}-2-(3H-imidazole-4-yl)-ethyl]-carbamic acid benzyl ester;

(S)-1-{[4-(2-Dimethylamino-ethoxy)-benzyl]-[(2-methyl-2-phenyl-propylcarbamoyl)-methyl]-carbamoyl}-2-(3H-imidazole-4-yl)-ethyl]-carbamic acid benzyl ester;

(2-(1H-Imidazol-4-yl)1-{isobutyl-[(2-methyl-2-phenyl-propyl carbamoyl)-methyl]-carbamoyl}-ethyl)-carbamic acid benzyl ester;

(S)-[1-((4-Benzyloxy-benzyl)-{[(1-phenyl-cyclobutylmethyl)-carbamoyl]-methyl}-carbamoyl)-2-(1H-imidazol-4-yl)-ethyl]-carbamic acid benzyl ester;

(S)-1-((4-Benzyloxy-benzyl)-{[(1-phenyl-cyclopropylmethyl)-carbamoyl]-methyl}-carbamoyl)-2-(1H-imidazol-4-yl)-ethyl]-carbamic acid benzyl ester;

(S)-[1-((4-Benzyloxy-benzyl)-{[(1-phenyl-cyclopentylmethyl)-carbamoyl]-methyl}-carbamoyl)-2-(1H-imidazol-4-yl)-ethyl]-carbamic acid benzyl ester;

(S)-1-((4-Phenyl-benzyl)-{[(1-phenyl-cyclobutylmethyl)-carbamoyl]-methyl}-carbamoyl)-2-(1H-imidazol-4-yl)-ethyl]-carbamic acid benzyl ester;

(S)-1-((4-Methoxy-benzyl)-{[(1-phenyl-cyclobutylmethyl)-carbamoyl]-methyl}-carbamoyl)-2-(1H-imidazol-4-yl)-ethyl]-carbamic acid benzyl ester;

(S)-1-((4-Methyl-benzyl)-{[(1-phenyl-cyclobutylmethyl)-carbamoyl]-methyl}-carbamoyl)-2-(1H-imidazol-4-yl)-ethyl]-carbamic acid benzyl ester;

(S)-N-(4-Benzyloxy-benzyl)-2-(3-benzyl-ureido)-3-(1H-imidazol-4-yl)-N-{[(1-phenyl-cyclobutylmethyl)-carbamoyl]-methyl}-propionamide;

(S)-2-(3-Benzyl-3-methyl-ureido)-N-(4-benzyloxy-benzyl)-3-(1H-imidazol-4-yl)-N-{[(1-phenyl-cyclobutylmethyl)-carbamoyl]-methyl}-propionamide;

(S)-1-((4-Benzyloxy-benzyl)-{[(1-phenyl-cyclobutylmethyl)-carbamoyl]-methyl}-carbamoyl)-2-(1H-imidazol-4-yl)-ethyl]-thiocarbamic acid S-benzyl ester;

(S)-(2-(1H-Imidazol-4-yl)-1-{{[(1-phenyl-cyclobutylmethyl)-carbamoyl]-methyl}-[4-(pyridin-2-ylmethoxy)-benzyl]-carbamoyl}-ethyl)-carbamic acid benzyl ester;

(S)-(1-((Cyclohexyl-methyl)-{[(-phenyl-cyclobutylmethyl)-carbamoyl]-methyl}-carbamoyl)-2-(1H-imidazol-4-yl)-ethyl]-carbamic acid benzyl ester;

(S)-(1-((Isobutyl)-{[(1-phenyl-cyclobutylmethyl)-carbamoyl]-methyl}-carbamoyl)-2-(1H-imidazol-4-yl)-ethyl]-carbamic acid benzyl ester;

N-[(Phenylmethoxy)carbonyl]-L-histidyl-N-[2-(phenylmethoxy)ethyl]-$N^2$-[[4-(phenylmethoxy)phenyl]methyl]glycinamide;

N-[(Phenylmethoxy)carbonyl]-L-histidyl-$N^2$-[(1,1'-biphenyl)-4-ylmethyl]-N-[2-(phenylmethoxy)ethyl]glycinamide;

N-[N-[N-[(Phenylmethoxy)carbonyl]-L-histidyl]-N-[[4-(phenylmethoxy)phenyl]methyl]glycyl]glycine phenylmethyl ester;

N-[(Phenylmethoxy)carbonyl]-L-histidyl-N-(4-phenylbutyl)-$N^2$-[[4-(phenylmethoxy)phenyl]methyl]glycinamide;

N-[(Phenylmethoxy)carbonyl]-L-histidyl-N-(3-phenoxypropyl)-$N^2$-[[$^4$-(phenylmethoxy)phenyl]methyl]glycinamide;

(S)-[1-(1H-Imidazol-3-ylmethyl)-2-oxo-2-[[2-(phenylmethoxy)ethyl][4-(phenylmethoxy)phenyl]methyl]amino]ethyl]carbamic acid, phenylmethyl ester; and

[1-(1H-Imidazol-4-ylmethyl)-2-oxo-2-[1,2,3,4-tetrahydro-7-(phenylmethoxy)-3-[[2-(phenylmethoxy)ethyl]amino]carbonyl]-2-isoquinolinyl]ethyl]carbamic acid, phenylmethyl ester.

DETAILED DESCRIPTION OF THE INVENTION

The present invention provides a combination of (1) compounds that inhibit protein farnesyltransferase (PFT); and (2) compounds that inhibit HMG CoA reductase.

While not intending to be limited by theory, it is believed by the inventors that a therapeutic synergy results from the administration of a combination of the compounds of Formulas I, II, III, IV, V, VI, VII, VIII, IX, and/or X which have an inhibitory action on PFT and compounds that have an inhibitory action on HMG CoA reductase. As discussed above, farneslyation of activated ras oncogene product by PFT is a critical step for its oncogenic function. It has been discovered that certain PFT inhibitors inhibit PFT in an FPP-competitive manner. Because HMG CoA reductase inhibitors, like lovastatin, reduce the cellular FPP pool, the HMG CoA reductase inhibitors have been found to ameliorate the activity of these FPP-competitive inhibitors.

Synthesis of FPP is dependent upon the enzymatic activity of HMG CoA reductase. It is believed that an inhibitor of HMG CoA reductase will decrease the availability of FPP, a necessary substrate for PFT leading to uncontrolled cell growth and reproduction. The combination of FPP-competitive PFT and HMG CoA reductase inhibitors, therefore, is believed to have an effect on diseases characterized by uncontrolled cell growth and reproduction, like cancer, restenosis and proliferative vascular disorders.

Compounds that inhibit HMG CoA reductase are known to those of skill in the art. HMG CoA reductase inhibitors of the present invention include, but are not limited to the following compounds: lovastatin, pravastatin, velostatin, atorvastatin, cerivastatin, simvastatin and the like.

In one embodiment, the compounds that inhibit PFT are those compounds that inhibit PFT in an FPP-dependent manner and/or are cell permeable. In preferred embodiments, the compounds that inhibit PFT are those compounds set forth in the summary of the invention.

The term "alkyl" means a straight or branched hydrocarbon having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "cycloalkyl" means a saturated hydrocarbon ring which contains from 3 to 7 carbon atoms, for example, cyclopropyl, cyclobutyl, cyclopentyl, cyclohexyl, adamantyl, and the like.

The term "aryl" means an aromatic ring which is a phenyl, 5-fluorenyl, 1-naphthyl, or 2-naphthyl group, unsubstituted or substituted by 1 to 3 substituents selected from alkyl, O-alkyl and S-alkyl, OH, SH, F, Cl, Br, I, $CF_3$, $NO_2$, $NH_2$, $NHCH_3$, $N(CH_3)_2$, NHCO-alkyl, $(CH_2)_mCO_2H$, $(CH_2)_mCO_2$-alkyl, $(CH_2)_mSO_3H$, $(CH_2)_mPO_3H_2$, $(CH_2)_mPO_3(alkyl)_2$, $(CH_2)_mSO_2NH_2$, and $(CH_2)_mSO_2NH$-alkyl wherein alkyl is defined as above and m is 0, 1, 2, or 3.

The term "heteroaryl" means a heteroaromatic ring which is a 2- or 3-thienyl, 2- or 3-furanyl, 2-or 3-pyrrolyl, 2-, 3-, or 4-pyridyl, imidazolyl, 2-, 3-, 4-, 5-, 6-, or 7-indoxyl group, unsubstituted or substituted by 1 or 2 substituents from the group of substituents described above for aryl.

The symbol "-" means a bond.

The term "patient" means all animals including humans. Examples of patients include humans, cows, dogs, cats, goats, sheep, and pigs.

A "therapeutically effective amount" is an amount of any of the combinations set forth in the present invention that when administered to a patient ameliorates a symptom of a viral infection, restenosis, cancer, atherosclerosis, psoriasis, endometriosis, or prevents restenosis or atherosclerosis. A therapeutically effective amount of the combinations of PFT and HMG CoA reductase inhibitor of the present invention can be easily determined by one skilled in the art by administering a quantity of a compound to a patient and observing the result. In addition, those skilled in the art are familiar with identifying patients having cancer, viral infections, restenosis, atherosclerosis, psoriasis, or endometriosis or who are at risk of having restenosis or atherosclerosis.

The term "cancer" includes, but is not limited to, the following cancers:

breast;

ovary;

cervix;

prostate;

testis;

esophagus;

glioblastoma;

neuroblastoma;

stomach;

skin, keratoacanthoma;

lung, epidermoid carcinoma, large cell carcinoma, adenocarcinoma;

bone;

colon, adenocarcinoma, adenoma;

pancreas, adenocarcinoma;

thyroid, follicular carcinoma, undifferentiated carcinoma, papillary carcinoma;

seminoma;

melanoma;

sarcoma;

bladder carcinoma;

liver carcinoma and biliary passages;

kidney carcinoma;

myeloid disorders;

lymphoid disorders, Hodgkins, hairy cells;

buccal cavity and pharynx (oral), lip, tongue, mouth, pharynx;

small intestine;

colon-rectum, large intestine, rectum;

brain and central nervous system; and leukemia.

The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgement, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laureate, borate, benzoate, lactate, phosphate, tosylate, citrate, maleate, fumarate, succinate, tartrate, naphtholate mesylate, glucoheptonate, lactobionate and laurylsulphonate salts, and the like. These may include cations based on the alkali and alkaline earth metals, such as sodium, lithium, potassium, calcium, magnesium and the like, as well as nontoxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, S. M. Berge, et al., "Pharmaceutical Salts," *J. Pharm. Sci,* 1977;66:1–19 which is incorporated herein by reference.)

Examples of pharmaceutically acceptable, non-toxic esters of the compounds of this invention include $C_1$–$C_6$ alkyl esters wherein the alkyl group is a straight or branched chain. Acceptable esters also include $C_5$–$C_7$ cycloalkyl esters as well as arylalkyl esters such as, but not limited to benzyl. $C_1$–$C_4$ alkyl esters are preferred. Esters of the compounds of the present invention may be prepared according to conventional methods.

Examples of pharmaceutically acceptable, non-toxic amides of the compounds of this invention include amides derived from ammonia, primary $C_1$–$C_6$ alkyl amines and secondary $C_1$–$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$–$C_3$ alkyl primary amines and $C_1$–$C_2$ dialkyl secondary amines are preferred. Amides of the compounds of the invention may be prepared according to conventional methods.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol 14 of the A.C.S. Symposium Series, and in *Bioreversible Carriers in Drug Design,* ed. Edward B. Roche, American Pharmaceutical Association and Pergamon Press, 1987, both of which are hereby incorporated by reference.

The combinations of compounds of the present invention can be administered to a patient alone or as part of a composition that contains other components such as excipients, diluents, and carriers, all of which are well-known in the art. The compositions can be administered to humans and animals either orally, rectally, parenterally (intravenously, intramuscularly or subcutaneously), intracisternally, intravaginally, intraperitoneally, intravesically, locally (powders, ointments or drops), or as a buccal or nasal spray.

Compositions suitable for parenteral injection may comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), Cremophor EL (a derivative of castor oil and ethylene oxide; purchased from Sigma Chemical Co., St. Louis, Mo.) and suitable mixtures thereof, vegetable oils (such as olive oil), and injectable organic esters such as ethyl oleate. Proper fluidity can be maintained, for example, by the use of a coating such as lecithin, by the maintenance of the required particle size in the case of dispersions and by the use of surfactants.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monostearate and gelatin.

Solid dosage forms for oral administration include capsules, tablets, pills, powders, and granules. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol, and silicic acid; (b) binders, as for example, carboxymethylcellulose, alignates, gelatin, polyvinylpyrrolidone, sucrose, and acacia; (c) humectants, as for example, glycerol; (d) disintegrating agents, as for example, agar—agar, calcium carbonate, potato or tapioca starch, alginic acid, certain complex silicates, and sodium carbonate, (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate, or mixtures thereof. In the case of capsules, tablets, and pills, the dosage forms may also comprise buffering agents.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well-known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, Cremophor EL (a derivative of castor oil and ethylene oxide; purchased from Sigma Chemical Co., St. Louis, Mo.), polyethyleneglycols and fatty acid esters of sorbitan or mixtures of these substances, and the like.

Besides such inert diluents, the composition can also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal administrations are preferably suppositories which can be prepared by mixing the compounds of the present invention with suitable non-irritating excipients or carriers such as cocoa butter, polyethyleneglycol, or a suppository wax, which are solid at ordinary temperatures but liquid at body temperature and therefore, melt in the rectum or vaginal cavity and release the active component.

Dosage forms for topical administration of a compound of this invention include ointments, powders, sprays, and inhalants. The active component is admixed under sterile conditions with a physiologically acceptable carrier and any preservatives, buffers, or propellants as may be required. Ophthalmic formulations, eye ointments, powders, and solutions are also contemplated as being within the scope of this invention.

The above farnesyl protein transferase compounds to be employed in combination with the HMG CoA reductase inhibitors set forth above will be used in therapeutic amounts as indicated in the Physicians' Desk Reference (PDR) 47$^{th}$ Edition (1993), which is incorporated herein by reference, or such therapeutically useful amounts as would be known to one of ordinary skill in the art.

The combinations can be administered at the recommended maximum clinical dosage or at lower doses. Dosage levels of the active compounds in the compositions of the invention may be varied so as to obtain a desired therapeutic response depending on the route of administration, severity of the disease and the response of the patient. The determination of optimum dosages for a particular patient is well known to those skilled in the art. The combination can be administered as separate compositions or as a single dosage form containing both agents.

The combinations of compounds of the present invention can be administered to a patient at dosage levels in the range of about 0.01 to about 2000 mg per day of PFT inhibitor and about 0.1 to about 500 mg per day of HMG CoA reductase inhibitor. The specific dosage used, however, can vary.

The compounds comprising the combinations of the present invention can exist in different stereoisomeric forms by virtue of the presence of asymmetric centers in the compounds. It is contemplated that all stereoisomeric forms of the compounds as well as mixtures thereof, including racemic mixtures, form part of this invention.

In addition, the compounds of the combinations of the present invention can exist in unsolvated as well as solvated forms with pharmaceutically acceptable solvents such as water, ethanol, and the like. In general, the solvated forms are considered equivalent to the unsolvated forms for the purposes of the present invention.

The examples presented below are intended to illustrate particular embodiments of the invention, and are not intended to limit the scope of the specification or the claims in any way.

EXAMPLES

Example 1

A proliferation assay was performed to ascertain the toxicity of a combination of a farnesyl protein transferase and lovastatin at various concentrations to a number of cancerous cell lines. The assay was also performed to ascertain the toxicity of the farnesyl protein transferase alone as a comparison against the combination.

Assay

Cell lines (Panc-1, Colon26, HT-29 Colon, H460 Lung, H-ras NIH 3T3 fibroblast, P388/ADR leukemia, and P388/S leukemia) were set up at various starting concentrations in 24- or 12-well dishes. Suspension cells were treated immediately; attached monolayer cells were allowed to attach for 24 hours prior to treatment. The cells were treated in one series of tests with lovastatin and solvent (DMSO); in another series of tests with a combination of lovastatin, solvent (DMSO) and the farnesyltransferase inhibitor, (S)-[1-{(4-benzyloxy-benzyl)-[(2-methyl-2-phenyl-propyl carbamoyl)-methyl]-carbamoyl}-2-(3H1-imidazol-4-yl)-ethyl]-carbamic acid benzyl ester (Compound A); and in a third series of cells were treated with only the farnesyltransferase inhibitor. After 72 hours of treatment, the cells (growing in 1 mL of medium) are trypsinized with warm (37 degrees celsius) trypsin-EDTA (0.5 mL for 1–2 minutes), agitated, rescued with 0.5 mL of warm (37) medium, then diluted in 9 mL Isoton (isotonic saline) for a final volume of 10 mL, 0.5 mL are then counted on a Coulter cell counter.

The data collected as IC$_{50}$ (concentration at which growth (cell#) is reduced by 50% relative to solvent (DMSO) treated controls) is set forth below in Table 1. The data for lovastatin treatment alone is relative to the DMSO-treated controls; the data for combination treatment is relative to the PFT inhibitor treatment alone samples.

TABLE 1

| | IC$_{50}$ ($\mu$M) | |
| --- | --- | --- |
| Cell Line | Lovastatin Only | Lovastatin + PD 169451 (10 $\mu$M) |
| P388/S | 4.0 | 0.28 |
| P388/ADR | 10.7 | 1.7 |
| Panc-1 | 18.8 | 15.4 |
| Colon26 | 1.2 | <0.3 |
| HT-29 colon | 11.4 | 2.6 |
| H460 lung | 5.5 | 0.95 |
| H-ras NIH 3T3 fibroblasts | 17.4 | 1.3$^a$ |

$^a$1 $\mu$M Compound A

The data demonstrates that the combination of the PFT inhibitor and lovastatin is a valuable inhibitor of cancerous cell growth which may be used in the medical treatment of tissue proliferative diseases, including cancer and restenosis. A synergistic reduction cell growth is achieved by exposure of the cell lines the PFT inhibitor rather than individual exposure of the cell lines to either lovastatin or the PFT inhibitor.

What is claimed is:

1. A combination of a compound having the Formula I

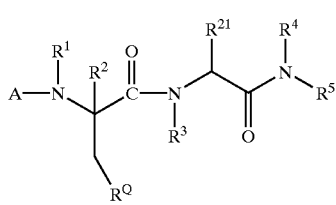

wherein

R$^{21}$ is hydrogen or C$_1$–C$_6$ alkyl;

$R^Q$ is

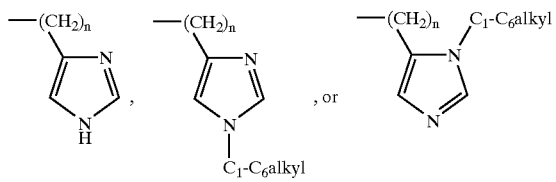

$n$ is 0 or 1;

A is —COR$^a$, —CO$_2$R$^{a'}$, —CONHR$^{a'}$, —CSR$^a$, —C(S)OR$^{a'}$, —C(S)NHR$^{a'}$,

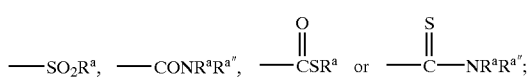

R$^a$, R$^{a'}$, and R$^{a''}$ are independently C$_1$–C$_6$ alkyl, —(CH$_2$)$_m$-cycloalkyl, —(CH$_2$)$_m$-aryl, or —(CH$_2$)$_m$-heteroaryl;

each $m$ is independently 0 to 3;

R$^1$, R$^2$, and R$^4$ are independently hydrogen or C$_1$–C$_6$ alkyl;

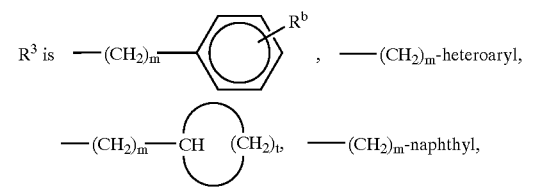

—(CH2)m-(heteroaryl substituted with R$^b$), or C$_1$–C$_6$ alkyl;

$t$ is 2 to 6;

R$^b$ is —O-phenyl, —O-benzyl, halogen, C$_1$–C$_6$ alkyl, hydrogen, —OC$_1$–C$_6$ alkyl, —NH$_2$, —NHR$^a$, NR$^a$R$^{a'}$,

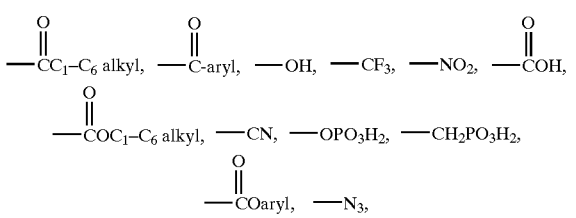

—CF$_2$CF$_3$, —SO$_2$R$^a$, —SO$_2$NR$^a$R$^{a'}$, —CHO, —OCOCH$_3$,

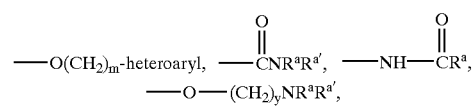

—O—(CH$_2$)$_m$-cycloalkyl, —(CH$_2$)$_m$-cycloalkyl, —O—(CH$_2$)$_m$-aryl, —(CH$_2$)$_m$-aryl, or —(CH$_2$)$_m$-heteroaryl;

$y$ is 2 or 3;

$R^5$ is

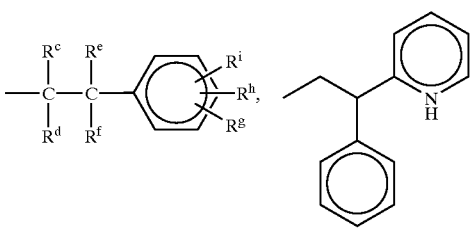

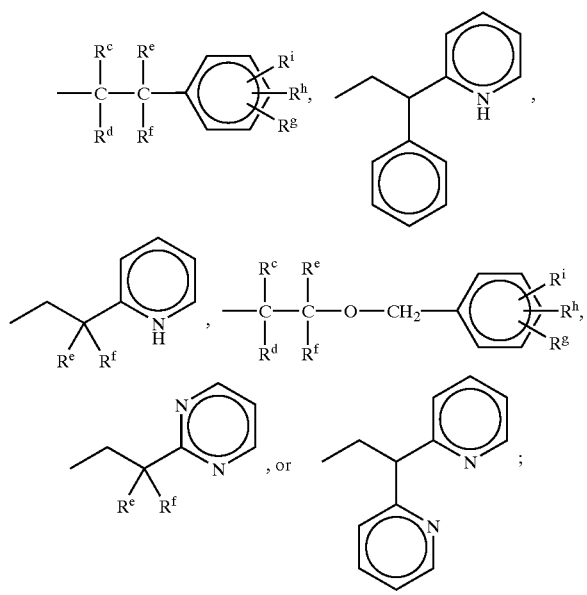

R$^i$, R$^g$, and R$^h$ are independently hydrogen, halogen, —OC$_1$–C$_6$ alkyl,

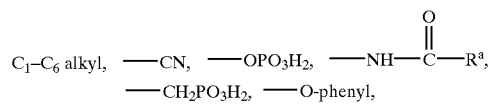

—O-benzyl, —NH$_2$, —NHR$^a$, —O—(CH$_2$)$_y$NR$^a$R$^{a'}$, —NR$^a$R$^{a'}$,

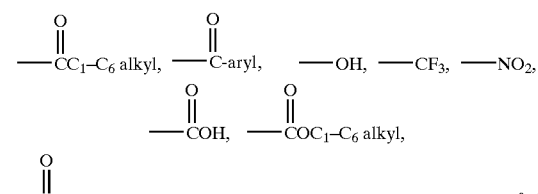

—OCOCH$_3$; and

R$^c$, R$^d$, R$^e$, and R$^f$ are independently C$_1$–C$_6$ alkyl, —(CH$_2$)$_m$-phenyl, hydrogen, —(CH$_2$)$_m$—OH, —(CH$_2$)$_m$NH$_2$, —(CH$_2$)$_m$-cycloalkyl, or —CN, and a compound having HMG CoA reductase inhibitory activity, and the pharmaceutically acceptable salts, esters, amides, and prodrugs of each compound thereof.

2. A combination in accordance with claim 1 wherein R$^1$ is hydrogen, R$^2$ is hydrogen, R$^4$ is hydrogen, R$^{21}$ is hydrogen or CH$_3$, and A is

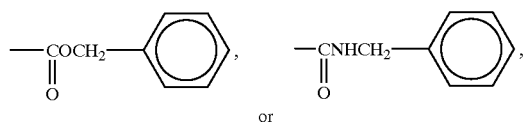

or

-continued

—C(=O)—N(C₁-C₆alkyl)—CH₂—phenyl.

3. A combination in accordance with claim 1 wherein R³ is

—(CH₂)$_m$—phenyl-R$^b$,   —(CH₂)$_m$—cyclohexyl,   or

—CH₂—CH(CH₃)₂

R¹ is hydrogen, R² is hydrogen, R⁴ is hydrogen, and R²¹ is hydrogen or CH₃.

4. A combination according to claim 1 wherein R⁵ is

—CH₂CH₂O—CH₂—phenyl,

—CH₂—CH(CH₃)—phenyl-R$^i$,

—CH₂CH₂-pyridyl (propyl-pyridyl variant),

—C(CH₃)₂—CH₂CH₃ substituted phenyl-R$^i$,

—C(CH₃)(CH₂CH₃)— attached to phenyl with CH₃,

—C(CH₃)₂—CH₂CH₃ substituted pyridyl,

—CH(CH₃)—CH₂CH₃ substituted pyridyl-CH₃,

—CH₂—CH(phenyl)—phenyl,   or   —CH₂CH₂—phenyl-R$^i$;

where R$^i$ is hydrogen, Cl, Br, F, or NH₂.

5. A combination of a compound having the Formula II

II

[Formula II structure with R⁶, R⁷, R²¹, R¹⁰, R¹¹, R¹², R¹³, R¹⁴, R⁸ substituents]

wherein

R⁶ is —O-benzyl, —NH-benzyl, or   —N(C₁-C₆ alkyl)-benzyl;

R²¹ is hydrogen or methyl;

R⁷ is hydrogen or methyl;

R⁸ is hydrogen, halogen, C₁-C₆ alkyl, —O-benzyl, —OC₁-C₆ alkyl, —CF₃, —OH, or —O—(CH₂)$_m$-pyridyl, or phenyl;

R¹⁰, R¹¹, R¹³, and R¹⁴ are independently hydrogen, C₁-C₆ alkyl, or —(CH₂)$_m$-phenyl;

each m is independently 0 to 3;

R¹² is

—phenyl(R$^j$,R$^k$,R$^l$),   —OCH₂-phenyl(R$^j$,R$^k$,R$^l$),   or

—pyridyl(R$^j$,R$^k$,R$^l$);   and

R$^j$, R$^k$, and R$^l$ are independently hydrogen, halogen, —OC₁-C₆ alkyl or C₁-C₆ alkyl, —NHR$^a$, NH₂, and a compound having HMG CoA reductase inhibitory activity, and the pharmaceutically acceptable salts, esters, amides, and prodrugs of each compound thereof.

6. A combination in accordance with claim 5 wherein R¹¹ and R¹⁴ are methyl.

7. A combination in accordance with claim 5 wherein R⁸ is methyl or methoxy.

8. A combination of a compound having the Formula III

III

[Formula III structure with X, R¹⁵, R¹⁶ substituents]

wherein

X is NH, O, or —N(CH₃);

R¹⁵ is —O-benzyl, —CF₃, hydrogen, halogen, —OC₁-C₆ alkyl, phenyl, —O—(CH₂)$_m$-pyridyl, or C₁-C₆ alkyl;

m is 0 to 3; and

R¹⁶ is a phenyl, hydrogen, or C₁-C₆ alkyl, and a compound having HMG CoA reductase inhibitory activity, and the pharmaceutically acceptable salts, esters, amides, and prodrugs of each compound thereof.

9. A combination of a compound having the Formula IV

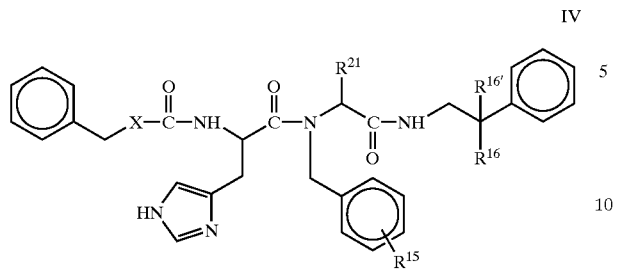

wherein

X is NH, O, or —N(CH₃);

R¹⁵ is —O-benzyl, —CF₃, hydrogen, halogen, C₁–C₆ alkylk —OC₁–C₆ alkyl, phenyl, or —O—(CH₂)ₘ-pyridyl;

R¹⁶ and R¹⁶' are C₁–C₆ alkyl;

m is 0 to 3; and

R²¹ is hydrogen or methyl, and a compound having HMG CoA reductase inhibitory activity, and the pharmaceutically acceptable salts, esters, amides, and prodrugs of each compound thereof.

10. A combination of a compound having the Formula V

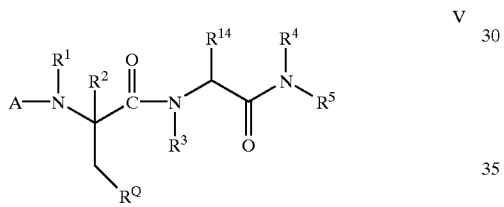

wherein

R_Q is

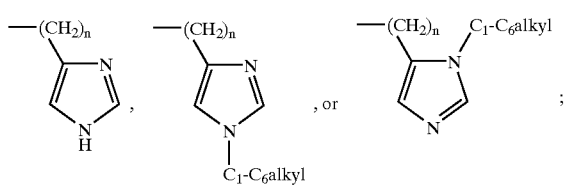

X is 0 or 1;

R¹⁴ is hydrogen or C₁–C₆ alkyl;

A is —COR^a, —CO₂R^a', —CONHR^a', —CSR^a,

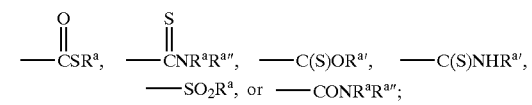

CONR^a R^a";

R^a, R^a', and R^a" are independently C₁–C₆ alkyl, —(CH₂)ₘ-cycloalkyl, —(CH₂)ₘ-aryl, or —(CH₂)ₘ-heteroaryl;

each m is independently 0 to 3;

R¹, R², and R⁴ are independently hydrogen or C₁–C₆ alkyl;

R₃ is 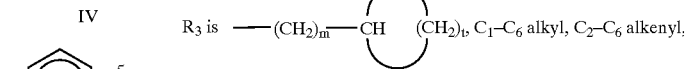

—(CH₂)ₘ-heteroaryl, —(CH₂)ₘ-naphthyl, —(CH₂)ₘ-(phenyl substituted with R^b), or —(CH₂)ₘ-(heteroaryl substituted with R^b);

t is 2 to 6;

R^b is —O—phenyl, —O-benzyl, halogen, C₁–C₆ alkyl, hydrogen,

—OC₁–C₆ alkyl, —NH₂, —NHR^a, —NR^a R^a',

—CC₁–C₆ alkyl(O), —C(O)—aryl, —OH, —CF₃,

—NO₂, —COH(O), —COC₁–C₆ alkyl(O), —CN,

—OPO₃H₂, —CH₂PO₃H₂, —CO aryl(O), —CNH₂(O),

—CNHR^a(O), —CNR^a R^a'(O), —NHCR^a(O)

—O(CH₂)y NR^a R^a', —N₃, —CF₂CF₃, —SO₂R^a,

—SO₂NR^a R^a', —CHO, —OCOCH₃, —O(CH₂)ₘ-heteroaryl, —O(CH₂)ₘ-aryl, —O(CH₂)ₘ-cycloalkyl, —(CH₂)ₘ-aryl, —(CH₂)ₘ-cycloalkyl, —(CH₂)ₘ-heteroaryl, or —CH=CHC₆H₅;

y is 2 or 3;

R⁵ is (phenyl substituted with R^g, R^h, and R^i)

or (heteroaryl substituted with R^g, R^h, and R^i)

each n is independently 2, 3, or 4;

R^i, R^g, and R^h are independently hydrogen, halogen, —OC₁–C₆ alkyl, C₁–C₆ alkyl, —CN, —OPO₃H₂, —CH₂PO₃H₂, —O-phenyl, —O-benzyl, —NH₂, —NHR^a, —NR^a R^a', —CC₁–C₆ alkyl(O), —C(O)—aryl, —CNH₂(O), CNHR^a(O), —CNHR^a R^a'(O), —NHCR^a(O), —O(CH₂)y NR^a R^a',

—OH, —CF₃, —NO₂, —COH(O),

-continued

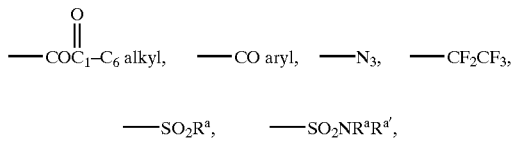

—CHO, or —OCOCH$_3$; and

R$^c$ and R$^d$ are independently C$_1$–C$_6$ alkyl, —(CH$_2$)$_m$-cycloalkyl or hydrogen, and a compound having HMG CoA reductase inhibitory activity, and the pharmaceutically acceptable salts, esters, amides, and prodrugs of each compound thereof.

11. A combination of a compound having the Formula VI

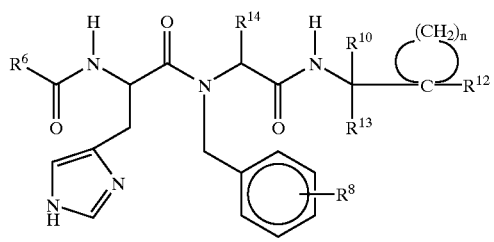

wherein
R$^6$ is —O-benzyl, —NH—benzyl, —N(C$_1$–C$_6$ alkyl)-benzyl, or —SCH$_2$-phenyl;
R$^8$ is hydrogen, halogen, C$_1$–C$_6$ alkyl, —O-benzyl, —OCH$_2$-pyridyl, —OC$_1$–C$_6$ alkyl, —CF$_3$, —OH, or -phenyl;
R$^{10}$ and R$^{13}$ are independently hydrogen or C$_1$–C$_6$ alkyl;
each n is independently 2, 3, or 4;
R$^{14}$ is hydrogen or methyl;

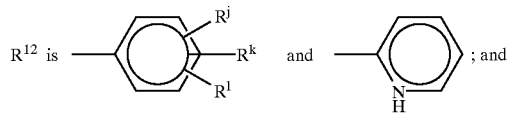

R$^j$, R$^k$, and R$^l$ are independently hydrogen, halogen, —NH$_2$, —NHR$^a$, —OC$_1$–C$_6$ alkyl, or —C$_1$–C$_6$ alkyl, and a compound having HMG CoA reductase inhibitory activity, and the pharmaceutically acceptable salts, esters, amides, and prodrugs of each compound thereof.

12. A combination of a compound having the Formula VII

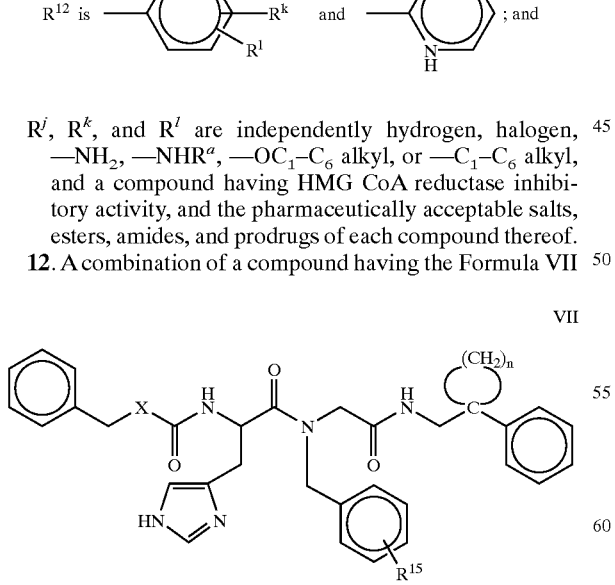

wherein
each n is 2, 3, or 4;

X is NH, O, or —NCH$_3$;
R$^{15}$ is —O-benzyl, —CF$_3$, hydrogen, halogen, —OH, -phenyl, —C$_1$–C$_6$ alkyl, —OCH$_2$-pyridyl, or —O$_{C1}$–C$_6$ alkyl, and a compound having HMG CoA reductase inhibitory activity, and the pharmaceutically acceptable salts, esters, amides, and prodrugs of each compound thereof.

13. A combination of a compound having the Formula VIII:

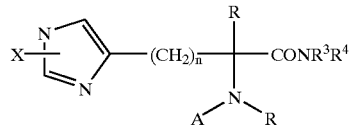

wherein:

n is 1 or 2;

A is COR$^2$, CO$_2$R$^2$, CONHR$^2$, CSR$^2$, C(S)OR$^2$, C(S)NHR$^2$, or SO$_2$R$^2$ with R$^2$ as defined below;

R is independently H or Me;

R$^2$ is alkyl, (CH$_2$)$_m$-cycloalkyl, (CH$_2$)$_m$-aryl, (CH$_2$)$_m$-heteroaryl with m is 0, 1, 2, or 3;

R$^3$ and R$^4$ is independently

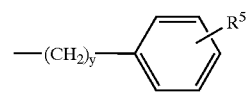

or (CH$_2$)$_n$CONH—R$^6$ with y is 1–5 and n as defined above and with R$^5$ and R$^6$ as defined below, or R$^3$ and R$^4$ are connected together to form a ring of the following type:

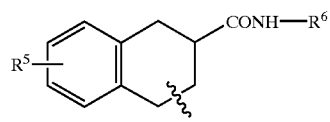

with R$^5$ and R$^6$ as defined below, or (CH$_2$)$_x$—R$^7$, with x is 2–5, and R$^7$ as defined below;

R$^5$ is R$^2$, OR$^2$, or SR$^2$ with R$^2$ as defined above;

R$^6$ is (CH$_2$)$_n$R$^5$, (CH$_2$)$_n$CO$_2$R$^2$, (CH$_2$)$_n$CONHR$^2$, (CH$_2$)$_n$CONH(CH$_2$)$_{n+1}$R$^5$, CH(COR$^8$)(CH$_2$)$_n$R$^5$, with n, R$^2$, and R$^5$ as defined above and R$^8$ as defined below;

R$^7$ is (CH$_2$)$_m$-cycloalkyl, (CH$_2$)$_m$-aryl, (CH$_2$)$_m$-heteroaryl, O(CH$_2$)$_m$-cycloalkyl, O(CH$_2$)$_m$-aryl, O(CH$_2$)$_m$-heteroaryl with m is 0, 1, 2, or 3;

R$^8$ is OH, O-alkyl, NH$_2$, or NH-alkyl; and

X is H, Me, (CH$_2$)$_n$CO$_2$R$^9$, or (CH$_2$)$_n$P(O)(OR$^9$)$_2$, with R$^9$ is H or alkyl;

and a compound having HMG CoA reductase inhibitory activity, and the pharmaceutically acceptable salts, esters, amides, and prodrugs of each compound thereof.

14. A combination of a compound having the Formula IX.

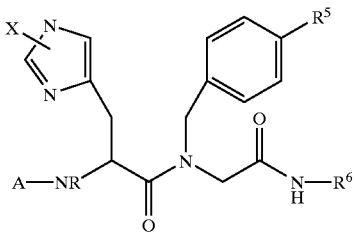

wherein:
A is limited to $CO_2R^2$, $CONHR^2$, $C(S)OR^2$, or $C(S)NHR^2$ with $R^2$ as defined below;
R is H or Me;
$R^2$ is limited to alkyl, $(CH_2)_m$-cycloalkyl, $(CH_2)_m$-aryl, $(CH_2)_m$-heteroaryl, with m is 0, 1, 2, or 3;
$R^5$ is limited to $(CH_2)_m$-aryl, O—$(CH_2)_m$-aryl, or O—$(CH_2)_m$-heteroaryl with m as defined above;
$R^6$ is limited to $CH_2$—$R^5$, $CH_2CO_2R^2$, $CH_2CONHR^2$, with n is 1 or 2, and with $R^5$ and $R^2$ as defined above; and
X is limited to H or Me;
and a compound having HMG CoA reductase inhibitory activity, and the pharmaceutically acceptable salts, esters, amides, and prodrugs of each compound thereof.

15. A combination of a compound having the Formula X:

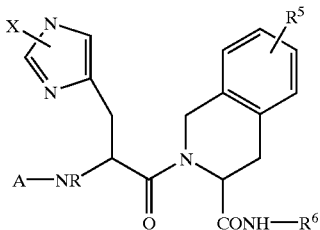

wherein:
A is limited to $CO_2R^2$, $CONHR^2$, $C(S)OR^2$, or $C(S)NHR^2$ with $R^2$ as defined below;
R is H or Me;
$R^2$ is limited to alkyl, $(CH_2)_m$-cycloalkyl, $(CH_2)_m$-aryl, $(CH_2)_m$-heteroaryl, with m is 0, 1, 2, or 3;
$R^5$ is limited to $(CH_2)_m$-aryl, O—$(CH_2)_m$-aryl, or O—$(CH_2)_m$-heteroaryl with m as defined above;
$R^6$ is limited to $CH_2$—$R^5$, $CH_2CO_2R^2$, $CH_2CONHR^2$, with n is 1 or 2, and with $R^5$ and $R^2$ as defined above; and
X is limited to H or Me;
and a compound having HMG CoA reductase inhibitory activity, and the pharmaceutically acceptable salts, esters, amides, and prodrugs of each compound thereof.

16. A combination according to claim 14 wherein:
A is further limited to $CO_2R^2$ or $CONHR^2$, with $R^2$ as defined below;
R is limited to H;
$R^2$ is further limited to alkyl, or $(CH_2)_m$-aryl with m is 0, 1, 2, or 3;
$R^5$ is further limited to $(CH_2)_m$-aryl or O—$(CH_2)_m$-aryl with m as defined above;

$R^6$ is limited to $CH_2$—$R^5$ or $CH_2CONHR^2$, with n is 1 or 2, and with $R^5$ and $R^2$ as defined above; and
X is limited to H or Me.

17. A combination according to claim 15 wherein:
A is further limited to $CO_2R^2$ or $CONHR^2$, with $R^2$ as defined below;
R is limited to H;
$R^2$ is further limited to alkyl, or $(CH_2)_m$-aryl with m is 0, 1, 2, or 3;
$R^5$ is further limited to $(CH_2)_m$-aryl or O—$(CH_2)_m$-aryl with m as defined above;
$R^6$ is limited to $CH_2$—$R^5$ or $CH_2CONHR^2$, with n is 1 or 2, and with $R^5$ and $R^2$ as defined above; and
X is limited to H or Me.

18. A pharmaceutically acceptable composition that comprises a combination of claim 1.

19. A pharmaceutically acceptable composition that comprises a combination of claim 10.

20. A pharmaceutically acceptable composition that comprises a combination of claim 13.

21. A method of treating or preventing restenosis, the method comprising administering to a patient having restenosis or at risk of having restenosis a therapeutically effective amount of a combination of claim 1, 10, or 13.

22. A method of treating or preventing cancer, the method comprising administering to a patient having cancer or at risk of having cancer a therapeutically effective amount of a combination of claim 1, 10, or 13.

23. The method of claim 22 wherein the cancer is lung cancer, colon cancer, pancreatic cancer, thyroid cancer, breast cancer, or bladder cancer.

24. A method of treating or preventing a viral infection, the method comprising administering to a patient having a viral infection or at risk of having a viral infection a therapeutically effective amount of a combination of claim 1, 10, or 13.

25. A method of treating or preventing psoriasis, the method comprising administering to a patient having psoriasis or at risk of having psoriasis a therapeutically effective amount of a combination of claim 1, 10, or 13.

26. The combination of a least one of the compounds:

(S)-[1-[(4-Benzyloxy-benzyl)-(phenethyl-carbamoyl-methyl)-carbamoyl]-2-(3H-imidazole-4-yl)-ethyl]-carbamic acid benzyl ester;

(S)-[1-[[2-Benzyloxy-ethylcarbamoyl]-methyl]-[4-chlorobenzyl]-carbamoyl]-2-(1H-imidazole-4-yl)-ethyl]-carbamic acid benzyl ester;

(S)-[1-[(4-Benzyloxy-benzyl)-[(2-phenyl-propyl-carbamoyl)-methyl]-carbamoyl]-2-(1H-imidazole-4-yl)-ethyl]carbamic acid benzyl ester;

(S)-[1-[(4-Benzyloxy-benzyl)-[(2,2-diphenyl-ethylcarbamoyl)-methyl]-carbamoyl]-2-(1H-imidazole-4-yl)-ethyl]-carbamic acid benzyl ester;

(S)-N-(4-Benzyloxy-benzyl)-2-(3-benzyl-ureido)-3-(1H-imidazole-4-yl)-N-[(2-phenyl-propylcarbamoyl)-methyl]-propionamide;

(S)-[1-{Biphenyl-4-ylmethyl-[(2-methyl-2-phenyl-propylcarbamoyl)-methyl]-carbamoyl}-2-(1H-imidazole-4-yl)-ethyl]-carbamic acid benzyl ester;

(S)-[1-{Biphenyl-4-ylmethyl-[(2-phenyl-propylcarbamoyl)-methyl]-carbamoyl}-2-(1H-imidazole4-yl)-ethyl]-carbamic acid benzyl ester;

(S)-[1-((4-Benzyloxy-benzyl)-{[2-(2-fluoro-phenyl)-ethylcarbamoyl]-methyl}-carbamoyl)-2-(1H-imidazole-4-yl)-ethyl]-carbamic acid benzyl ester;

(S)-[1-{(4-Benzyloxy-benzyl)-[(2-pyridin-2-yl-ethylcarbamoyl)-methyl]-carbamoyl}-2-(1H-imidazole-4-yl)-ethyl]-carbamic acid benzyl ester;
(S)-[1-((4-Benzyloxy-benzyl)-{[2-(2-bromo-phenyl)-ethylcarbamoyl]-methyl}-carbamoyl)-2-(1H-imidazole-4-yl)-ethyl]-carbamic acid benzyl ester;
(S)-[1-{(4-Benzyloxy-benzyl)-[(1-methyl-2-phenyl-ethylcarbamoyl)-methyl]-carbamoyl}-2-(1H-imidazole-4-yl)-ethyl]-carbamic acid benzyl ester;
(S)-[1-{(4-Benzyloxy-benzyl)-[(2-phenyl-2-pyridin-2-yl-ethylcarbamoyl)-methyl]-carbamoyl}-2-(1H-imidazole-4-yl)-ethyl]-carbamic acid benzyl ester;
(S)-[1-{(4-Chloro-benzyl)-[(2-phenyl-propylcarbamoyl)-methyl]-carbamoyl}-2-(1H-imidazole-4-yl)-ethyl]-carbamic acid benzyl ester;
(S)-[1-{(4-Benzyloxy-benzyl)-[(2-phenyl-butylcarbamoyl)-methyl]-carbamoyl}-2-(1H-imidazole-4-yl)-ethyl]-carbamic acid benzyl ester;
(S)-N-(4-Benzyloxy-benzyl)-3-(1H-imidazole-4-yl)-2-(3-phenyl-propionylamino)-N-[(2-phenyl-propylcarbamoyl)-methyl]-propionamide;
(S)-[1-{(4-Fluoro-benzyl)-[(2-phenyl-propylcarbamoyl)-methyl]-carbamoyl}-2-(1H-imidazole-4-yl)-ethyl]-carbamic acid benzyl ester;
(S)-(2-(1H-Imidazole4-yl)-1-{(4-methyl-benzyl)-[(2-phenyl-propylcarbamoyl)-methyl]-carbamoyl}-ethyl)-carbamic acid benzyl ester;
(S)-(2-(1H-imidazole-4-yl)-1-{(4-methoxy-benzyl)-[(2-phenyl-propylcarbamoyl)-methyl]-carbamoyl}-ethyl)-carbamic acid benzyl ester;
(S)-[1-[{[2-(2-Amino-phenyl)-propylcarbamoyl]-methyl}-(4-benzyloxy-benzyl)-carbamoyl]-2-(3H-imidazole-4-yl)-ethyl]-carbamic acid benzyl ester;
(S)-[1-{(4-Fluoro-benzyl)-[(2-methyl-2-phenyl-propylcarbamoyl)-methyl]-carbamoyl}-2-(1H-imidazole-4-yl)-ethyl]-carbamic acid benzyl ester;
(S)-[1-{Benzyl-[(2-phenyl-propylcarbamoyl)-methyl]-carbamoyl}-2-(1H-imidazole-4-yl)-ethyl]-carbamic acid benzyl ester;
(S)-[1-((4-Benzyloxy-benzyl)-{[2-(2-chloro-phenyl)-2-phenyl-ethylcarbamoyl]-methyl}-carbamoyl)-2-(1H-imidazole-4-yl)-ethyl]-carbamic acid benzyl ester;
(S)-[1{(4-Benzyloxy-benzyl)-[(2-ethyl-2-phenyl-butylcarbamoyl)-methyl]-carbamoyl}-2-(3H-imidazole-4-yl)-ethyl]-carbamic acid benzyl ester;
(S)-N-(4-Benzyloxy-benzyl)-2-(3-benzyl-ureido)-3-(1H-imidazole-4-yl)-N-[(2-phenyl-propylcarbamoyl)-methyl]-propionamide;
(S)-N-(4-Benzyloxy-benzyl)-2-(3-benzyl-ureido)-3-(1H-imidazole-4-yl)-N-[(2-phenyl-butylcarbamoyl)-methyl]-propionamide;
(S)-[1-{(2-Chloro-benzyl)-[(2-phenyl-propylcarbamoyl)-methyl]-carbamoyl}-2-(1H-imidazole-4-yl)-ethyl]-carbamic acid benzyl ester;
(S)-[1-{(4-Bromo-benzyl)-[(2-phenyl-propylcarbamoyl)-methyl]-carbamoyl}-2-(1H-imidazole-4-yl)-ethyl]-carbamic acid benzyl ester;
(S)-[1-{(3-Chloro-benzyl)-[(2-phenyl-propylcarbamoyl)-methyl]-carbamoyl}-2-(1H-imidazole-4-yl)-ethyl]-carbamic acid benzyl ester;
(S)-[1-{(4-Chloro-benzyl)-[(2-methyl-2-phenyl-propylcarbamoyl)-methyl]-carbamoyl}-2-(1H-imidazole4-yl)-ethyl]-carbamic acid benzyl ester;
(S)-[1-((4-Benzyloxy-benzyl)-{[2-(2-chloro-phenyl)-propylcarbamoyl]-methyl}-carbamoyl)-2-(1H-imidazole4-yl)-ethyl]-carbamic acid benzyl ester;
(S)-(2-(1H-Imidazole-4-yl)-1-{(2-methoxy-benzyl)-[(2-phenyl-propylcarbamoyl)-methyl]-carbamoyl}-ethyl)-carbamic acid benzyl ester;
(S)-(2-(1H-Imidazole-4-yl)-1-{[(2-phenyl-propylcarbamoyl)-methyl]-[4-(pyridin-4-ylmethoxy)-benzyl]-carbamoyl}-ethyl)-carbamic acid benzyl ester;
(S)-(2-(1H-Imidazole-4-yl)-1-{(3-methoxy-benzyl)-[(2-phenyl-propylcarbamoyl)-methyl]-carbamoyl}-ethyl)-carbamic acid benzyl ester;
(S)-(2-(1H-Imidazole-4-yl)-1-{[(2-phenyl-propylcarbamoyl)-methyl]-[4-(pyridin-3-ylmethoxy)-benzyl]-carbamoyl}-ethyl)-carbamic acid benzyl ester;
(S)-(2-(1H-Imidazole-4-yl)-1-{naphthalen-1-ylmethyl-[(2-phenyl-propylcarbamoyl)-methyl]-carbamoyl}-ethyl)-carbamic acid benzyl ester;
(S)-{2-(1H-Imidazole-4-yl)-1-[[(2-phenyl-propylcarbamoyl)-methyl]-(4-trifluoromethyl-benzyl)-carbamoyl]-ethyl}-carbamic acid benzyl ester;
(S)-(2-(1H-Imidazole-4-yl)-1-{[(2-methyl-2-phenyl-propylcarbamoyl)-methyl]-pyridin-3-ylmethyl-carbamoyl}-ethyl)-carbamic acid benzyl ester;
(S)-(2-(1H-Imidazole-4-yl)-1-{[(2-methyl-2-phenyl-propylcarbamoyl)-methyl]-[4-(pyridin-2-ylmethoxy)-benzyl]-carbamoyl}-ethyl)-carbamic acid benzyl ester;
(S)-[1-{Benzyl-[(2-methyl-2-phenyl-propylcarbamoyl)-methyl]-carbamoyl}-2-(1H-imidazole-4-yl)-ethyl]-carbamic acid benzyl ester;
(S)-(2-(1H-Imidazole-4-yl)-1-{(2-methyl-benzyl)-[(2-phenyl-propylcarbamoyl)-methyl]-carbamoyl}-ethyl)-carbamic acid benzyl ester;
(S)-(2-(1H-Imidazole-4-yl)-1-{(4-methoxy-benzyl)-[(2-methyl-2-phenyl-propylcarbamoyl)-methyl]-carbamoyl}-ethyl)-carbamic acid benzyl ester;
(S)-[1{(4-Benzyloxy-benzyl)-[(2-cyano-2-phenyl-ethylcarbamoyl)-methyl]-carbamoyl}-2-(1H-imidazole-4-yl)-ethyl]-carbamic acid benzyl ester;
(S)-(2-(1H-Imidazole-4-yl)-1-{[(2-methyl-2-phenyl-propylcarbamoyl)-methyl]-pyridin-2-ylmethyl-carbamoyl}-ethyl)-carbamic acid benzyl ester;
(S)-(2-(1H-Imidazole-4-yl)-1-{(3-methyl-benzyl)-[(2-phenyl-propylcarbamoyl)-methyl]-carbamoyl}-ethyl)-carbamic acid benzyl ester;
(S)-[1-{(4-Dimethylamino-benzyl)-[(2-phenyl-propylcarbamoyl)-methyl]-carbamoyl}-2-(1H-imidazole-4-yl)-ethyl]-carbamic acid benzyl ester;
(S)-(2-(1H-Imidazole-4-yl)-1-{[(2-methyl-2-phenyl-propylcarbamoyl)-methyl]-[4-(pyridin-4-ylmethoxy)-benzyl]-carbamoyl}-ethyl)-carbamic acid benzyl ester;
(S)-(2-(1H-Imidazole-4-yl)-1-{[(2-methyl-2-phenyl-propylcarbamoyl)-methyl]-[4-(pyridin-3-ylmethoxy)-benzyl]-carbamoyl}-ethyl)-carbamic acid benzyl ester;
(2-(1-H-imidazole-4-yl)-1-{isobutyl-[(2-phenyl-propylcarbamoyl)-methyl]-carbamoyl}-ethyl)-carbamic acid benzyl ester;
(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid benzyl ester;
(S)-2-(3-Benzyl-3-methyl-ureido)-N-(4-benzyloxy-benzyl)-3-(1H-imidazole-4-yl)-N-[(2-methyl-2-phenyl-propylcarbamoyl)-methyl]-propionamide;
(S)-[1-{(4-Benzyloxy-benzyl)-[(2-hydroxy-2-phenyl-ethylcarbamoyl)-methyl]-carbamoyl}-2-(3H-imidazole-4-yl)-ethyl]-carbamic acid benzyl ester;
(S)-(2-(1H-Imidazole-4-yl)-1-{(4-methoxy-benzyl)-[(2-phenyl-propylcarbamoyl)-methyl]-carbamoyl}-ethyl)-carbamic acid benzyl ester;
(S)-[1-((4-Benzyloxy-benzyl)-{[2-(2-chloro-phenyl)-ethylcarbamoyl]-methyl}-carbamoyl)-2-(1H-imidazole-4-yl)-ethyl]-carbamic acid benzyl ester;
(S)-[1-{(4-Benzyloxy-benzyl)-[(2-methyl-2-phenyl-propylcarbamoyl)-methyl]-carbamoyl}-2-(1H-imidazole-4-yl)-ethyl]-carbamic acid thiophen-3-ylmethyl ester;

(S)-[1-{(4-Chloro-benzyl)-[1-(2-methyl-2-phenyl-propylcarbamoyl)-ethyl]-carbamoyl}-2-(3H-imidazole-4-yl)-ethyl]-carbamic acid benzyl ester;

(S)-(2-(1H-Imidazole-4-yl)-1-{(4-methyl-benzyl)-[(2-methyl-2-phenyl-propylcarbamoyl)-methyl]-carbamoyl}-ethyl)-carbamic acid benzyl ester;

(S)-(2-(1H-Imidazole-4-yl)-1-{(2-methoxy-benzyl)-[(2-methyl-2-phenyl-propylcarbamoyl)-methyl]-carbamoyl}-ethyl)-carbamic acid benzyl ester;

(S)-2-(3-Benzyl-3-methyl-ureido)-N-(4-chloro-benzyl)-3-(1H-imidazole-4-yl)-N-[(2-methyl-2-phenyl-propylcarbamoyl)-methyl]-propionamide;

(S)-(2-(1H-Imidazole-4-yl)-1-{(3-methoxy-benzyl)-[(2-methyl-2-phenyl-propylcarbamoyl)-methyl]-carbamoyl}-ethyl)-carbamic acid benzyl ester;

(S)-(2-(1H-Imidazole-4-yl)-1-{[(2-methyl-2-phenyl-propylcarbamoyl)-methyl]-[2-(pyridin-4-ylmethoxy)-benzyl]-carbamoyl}-ethyl)-carbamic acid benzyl ester;

(S)-[1-{Cyclohexylmethyl-[(2-phenyl-propylcarbamoyl)-methyl]-carbamoyl}-2-(3H-imidazole-4-yl)-ethyl]-carbamic acid benzyl ester;

(S)-[1-{(4-Benzyloxy-benzyl)-[(2-phenyl-pentylcarbamoyl)-methyl]-carbamoyl}-2-(3H-imidazole-4-yl)-ethyl]-carbamic acid benzyl ester;

(S)-[1-{[2-(4-Benzyloxy-phenyl)-ethyl]-[(2-methyl-2-phenyl-propylcarbamoyl)-methyl]-carbamoyl}-2-(3H-imidazole-4-yl)-ethyl]-carbamic acid benzyl ester;

(S)-(2-(3H-Imidazole-4-yl)-1-{[2-(4-methoxy-phenyl)-ethyl]-[(2-methyl-2-phenyl-propylcarbamoyl)-methyl]-carbamoyl}-ethyl)-carbamic acid benzyl ester;

(S)-[1-[{[2-(2-Amino-phenyl)-ethylcarbamoyl]-methyl}-(4-benzyloxy-benzyl)-carbamoyl]-2-(3H-imidazole-4-yl)-ethyl]-carbamic acid benzyl ester;

(2-(1H-imidazol-4-yl)-1-{isobutyl-[(2-phenyl-propylcarbamoyl)-methyl]-carbamoyl}-ethyl)-carbamic acid benzyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-methyl-carbamic acid benzyl ester;

(S)-[1-{(4-Benzyloxy-benzyl)-[(2-methyl-2-phenyl-propylcarbamoyl)-methyl]-carbamoyl}-2-(3-methyl-3H-imidazole-4-yl)-ethyl]-carbamic acid benzyl ester;

(S)-[1-{(4-Benzyloxy-benzyl)-[(2-methyl-2-phenyl-propylcarbamoyl)-methyl]-carbamoyl}-2-(1-methyl-1H-imidazole-4-yl)-ethyl]-carbamic acid benzyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid furan-2-ylmethyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid thiophen-2-ylmethyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid pyridin-3-ylmethyl ester;

(S)-[1-{(4-Benzyloxy-benzyl)-[(2-methyl-2-phenyl-propylcarbamoyl)-methyl]-carbamoyl}-2-(3H-imidazole-4-yl)-ethyl]-carbamic acid 1H-imidazole-4-ylmethyl ester;

(S)-2-(3-Benzyl-ureido)-N-(4-chloro-benzyl)-3-(3H-imidazole-4-yl)-N-[(2-methyl-2-phenyl-propylcarbamoyl)-methyl]-propionamide;

(S)-[1{-(4-Benzyloxy-benzyl)-[(2-methyl-2-phenyl-propylcarbamoyl)-methyl]-carbamoyl}-2-(3H-imidazole-4-yl)-ethyl]-carbamic acid 4-methoxy-benzyl ester;

(S)-2-(3-Benzyl-thioureido)-3-(3H-imidazole-4-yl)-N-(4-methyl-benzyl)-N-[(2-methyl-2-phenyl-propylcarbamoyl)-methyl]-propionamide;

(S)-2-Acetylamino-N-(4-benzyloxy-benzyl)-3-(3H-imidazole-4-yl)-N-[(2-methyl-2-phenyl-propylcarbamoyl)-methyl]-propionamide;

(S)-(2-(3H-Imidazole-4-yl)-1-{[(2-methyl-2-phenyl-propylcarbamoyl)-methyl]-pyridin-4-ylmethyl-carbamoyl}-ethyl)-carbamic acid benzyl ester;

(S)-{2-(3H-Imidazole-4-yl)-1-[(4-iodo-benzyl)-(phenethylcarbamoyl-methyl)-carbamoyl]-ethyl}-carbamic acid benzyl ester;

(S)-[1-{(4-Amino-benzyl)-[(2-methyl-2-phenyl-propylcarbamoyl)-methyl]-carbamoyl}-2-(3H-imidazole-4-yl)-ethyl]-carbamic acid benzyl ester;

(S)-[1-{(4-Ethoxy-benzyl)-[(2-methyl-2-phenyl-propylcarbamoyl)-methyl]-carbamoyl}-2-(3H-imidazole-4-yl)-ethyl]-carbamic acid benzyl ester;

(S)-[1-{[4-(2-Dimethylamino-ethoxy)-benzyl-[(2-methyl-2-phenyl-propylcarbamoyl)-methyl]-carbamoyl}-2-(3H-imidazole-4-yl)-ethyl]-carbamic acid benzyl ester;

(2-(1H-Imidazol-4-yl)-1-{isobutyl-[(2-methyl-2-phenyl-propyl carbamoyl)-methyl]-carbamoyl}-ethyl)-carbamic acid benzyl ester;

(S)-[1-((4-Benzyloxy-benzyl)-{[(1-phenyl-cyclobutylmethyl)-carbamoyl]-methyl}-carbamoyl)-2-(1H-imidazol-4-yl)-ethyl-carbamic acid benzyl ester;

(S)-[1-((4-Benzyloxy-benzyl)-{[(1-phenyl-cyclopropylmethyl)-carbamoyl]-methyl}-carbamoyl)-2-(1H-imidazol-4-yl)-ethyl-carbamic acid benzyl ester;

(S)-[1-((4-Benzyloxy-benzyl)-{[(1-phenyl-cyclopentylmethyl)-carbamoyl]-methyl}-carbamoyl)-2-(1H-imidazol-4-yl)-ethyl-carbamic acid benzyl ester;

(S)-[1-((4-Phenyl-benzyl)-{[(1-phenyl-cyclobutylmethyl)-carbamoyl]-methyl}-carbamoyl)-2-(1H-imidazol-4-yl)-ethyl]-carbamic acid benzyl ester;

(S)-[1-((4-Methoxy-benzyl)-{[(1-phenyl-cyclobutylmethyl)-carbamoyl]-methyl}-carbamoyl)-2-(1H-imidazol-4-yl)-ethyl]-carbamic acid benzyl ester;

(S)-[1-((4-Methyl-benzyl)-{[(1-phenyl-cyclobutylmethyl)-carbamoyl]-methyl}-carbamoyl)-2-(1H-imidazol-4-yl)-ethyl]-carbamic acid benzyl ester;

(S)-N-(4-Benzyloxy-benzyl)-2-(3-benzyl-ureido)-3-(1H-imidazol-4-yl)-N-{[(1-phenyl-cyclobutylmethyl)-carbamoyl]-methyl}-propionamide;

(S)-2-(3-Benzyl-3-methyl-ureido)-N-(4-benzyloxy-benzyl)-3-(]H-imidazol-4-yl)-N-{[(1-phenyl-cyclobutylmethyl)-carbamoyl]-methyl}-propionamide;

(S)-[1-((4-Benzyloxy-benzyl)-{[(1-phenyl-cyclobutylmethyl)-carbamoyl]-methyl}-carbamoyl)-2-(1H-imidazol-4-yl)-ethyl]-thiocarbamic acid S-benzyl ester;

(S)-(2-(1H-Imidazol-4-yl)-1-{{[(1-phenyl-cyclobutylmethyl)-carbamoyl]-methyl}-[4-(pyridin-2-yl-methoxy)-benzyl]-carbamoyl}-ethyl)-carbamic acid benzyl ester;

(S)-(1-((Cyclohexyl-methyl)-{[(1-phenyl-cyclobutylmethyl)-carbamoyl]-methyl}-carbamoyl)-2-(1H-imidazol-4-yl)-ethyl]-carbamic acid benzyl ester;

(S)-(1-((Isobutyl)-{[(1-phenyl-cyclobutylmethyl)-carbamoyl]-methyl}-carbamoyl)-2-(1H-imidazol-4-yl)-ethyl]-carbamic acid benzyl ester;

N-[(Phenylmethoxy)carbonyl]-L-histidyl-N-[2-(phenylmethoxy)ethyl]-N$^2$-[[4-(phenylmethoxy)phenyl]methyl]glycinamide;

N-[(Phenylmethoxy)carbonyl]-L-histidyl-N$^2$-[(1,1'-biphenyl)-4-ylmethyl]-N-[2-(phenylmethoxy)ethyl] glycinamide;

N-[N-[N-[(Phenylmethoxy)carbonyl]-L-histidyl]-N-[[4-(phenylmethoxy)phenyl]methyl]glycyl]glycine phenylmethyl ester;

N-[(Phenylmethoxy)carbonyll-L-histidy]-N-(4-phenylbutyl)-$N^2$-[[4-(phenylmethoxy)phenyl]methyl]glycinamide;

N-[(Phenylmethoxy)carbonyl]-L-histidyl-N-(3-phenoxypropyl)-$N^2$-[[4-(phenylmethoxy)phenyl]methyl]glycinamide;

(S)-[1-(1H-Imidazol-3-ylmethyl)-2-oxo-2-[[2-(phenylmethoxy)ethyl][4-(phenylmethoxy)phenyl]methyl]amino]ethyl]carb amic acid, phenylmethyl ester; or

[-(1H-Imidazol-4-ylmethyl)-2-oxo-2-[1,2,3,4-tetrahydro-7-(phenylmethoxy)-3-[[2-(phenylmethoxy)ethyl]amino]carbonyl]-2-isoquinolinyl]ethyl]carbamic acid, phenylmethyl ester;

and at least one HMG CoA reductase inhibitor.

27. The combination of claim 26 wherein the HMG CoA reductase inhibitor is lovastatin.

28. The combination of claim 26 wherein the HMG CoA reductase inhibitor is atorvastatin.

29. The combination of claim 27 wherein the compound is (S)-[1-{(4-Benzyloxy-benzyl)-[(2-methyl-2-phenyl-propylcarbamoyl)-methyl]-carbamoyl}-2-(3H-imidazol-4-yl)-ethyl]-carbamic acid benzyl ester.

30. The combination of claim 28 wherein the compound is (S)-[1-{(4-Benzyloxy-benzyl)-[(2-methyl-2-phenyl-propylcarbamoyl)-methyl]-carbamoyl}-2-(3H-imidazol-4-yl)-ethyl]-carbamic acid benzyl ester.

* * * * *

UNITED STATES PATENT AND TRADEMARK OFFICE
CERTIFICATE OF CORRECTION

PATENT NO. : 6,492,410 B1  Page 1 of 1
DATED : December 10, 2002
INVENTOR(S) : Judith Leopold et al.

It is certified that error appears in the above-identified patent and that said Letters Patent is hereby corrected as shown below:

Column 29,
Line 18, "alkylk – $OC_1$ – $C_6$ alkyl, phenyl, or – O – $(CH_2)_m$ –", should read
-- alkyl – $OC_1$ – $C_6$ alkyl, phenyl, or – O – $(CH_2)_m$ – --.
Line 42, "—$(CH_2)_n$   —$(CH_2)_n$   —$(CH_2)_n$   $C_1$-$C_6$alkyl",
should read -- —$(CH_2)_x$   —$(CH_2)_x$   —$(CH_2)_x$   $C_1$-$C_6$alkyl --.

Column 31,
Line 3,     O                              O            O
       "    ||    ", should read "        ||           ||    ".

Column 32,
Line 5, "—$O_{C1}$ –$C_6$alkyl, and a compound having HMG CoA", should read
-- —$OC_1$ –$C_6$ alkyl, and a compound having HMG CoA --.

Column 38,
Line 43, "3-(]H-imidazol-4-yl)-N-{[(1-pheny-cyclobutylmethyl)-", should read
-- 3-(1H-imidazol-4-yl)-N-{[(1-pheny-cyclobutylmethyl)- --.

Column 39,
Line 9, "methyl]amino]ethyl]carb amic acid, phenylmethyl ester;", should read
-- methyl]amino]ethyl]carbamic acid, phenylmethyl ester --.

Signed and Sealed this

Seventeenth Day of February, 2004

JON W. DUDAS
*Acting Director of the United States Patent and Trademark Office*